United States Patent [19]

Khanna et al.

[11] Patent Number: 5,227,384
[45] Date of Patent: * Jul. 13, 1993

[54] 5-SUBSTITUTED [4,5-C] IMIDAZOPYRIDINES AND PHARMACEUTICAL USE THEREOF

[75] Inventors: Ish K. Khanna, Vernon Hills; Roger Nosal, Buffalo Grove; Richard M. Weier, Lake Bluff, all of Ill.

[73] Assignee: G. D. Searle & Co., Chicago, Ill.

[*] Notice: The portion of the term of this patent subsequent to Apr. 3, 2007 has been disclaimed.

[21] Appl. No.: 670,133

[22] Filed: Mar. 15, 1991

Related U.S. Application Data

[63] Continuation-in-part of Ser. No. 317,871, Mar. 6, 1989, Pat. No. 5,019,581, which is a continuation-in-part of Ser. No. 167,671, Mar. 14, 1988, Pat. No. 4,914,108.

[51] Int. Cl.$^5$ .................. A61K 31/435; C07D 471/04
[52] U.S. Cl. ..................................... 514/303; 546/118
[58] Field of Search .......................... 546/118; 514/303

[56] References Cited

U.S. PATENT DOCUMENTS

| | | | |
|---|---|---|---|
| 4,327,100 | 4/1982 | Austel et al. | 546/118 |
| 4,336,257 | 6/1982 | Baldwin | 546/118 |
| 4,914,108 | 4/1990 | Khanna et al. | 546/118 |
| 5,019,581 | 5/1991 | Khanna et al. | 546/118 |

FOREIGN PATENT DOCUMENTS 0260613 3/1988 European Pat. Off.

*Primary Examiner*—C. Warren Ivy
*Assistant Examiner*—James H. Turnipseed
*Attorney, Agent, or Firm*—Joy Ann Serauskas; Paul D. Matukaitis

[57] ABSTRACT

The present invention relates to a class of compounds represented by the formula

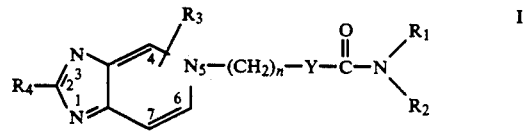

or a pharmaceutically acceptable salt thereof useful in the treatment of diseases or disorders mediated by platelet activating factor (PAF).

6 Claims, No Drawings

5-SUBSTITUTED [4,5-C] IMIDAZOPYRIDINES AND PHARMACEUTICAL USE THEREOF

This application is a continuation-in-part of Ser. No. 07/317,871, filed Mar. 6, 1989, now U.S. Pat. No. 5,019,581 which is a continuation-in-part of Ser. No. 07/167,671, filed Mar. 14, 1988, now U.S. Pat. No. 4,914,108.

FIELD OF THE INVENTION

This invention is in the field of mammalian therapeutics and relates to compounds for treatment of mammalian diseases such as inflammation, cardiovascular disorders, asthma and other diseases. Of particular interest is a class of 5-substituted [4,5-c] imidazopyridines useful for treatment of cardiovascular and immuno-inflammatory related disorders mediated by platelet activating factor (PAF).

BACKGROUND OF THE INVENTION

Platelet-activating factor (PAF) has been associated with various biological activities and pathways, thus making it an important mediator responsible for a variety of physiological processes including, but not limited to, activation and aggregation of platelets, smooth muscle contraction, pathogenesis of immune complex deposition, inflammation, immunomodulation, respiratory, cardiovascular and intravascular alterations. These physiological processes are associated with a large group of diseases, such as, for example, cardiovascular disorders, asthma, lung edema, endotoxin shock, adult respiratory distress syndrome and inflammatory diseases, autoimmunization and graft rejection.

U.S. Pat. No. 4,804,658 discloses a class of imidazopyridine derivatives useful in the treatment of diseases or disorders mediated by platelet-activating factor. The present invention is distinct from this disclosure in that in the present invention the benzamide moiety is attached to the nitrogen (position 5) which makes up the six membered ring of the imidazopyridine ring system as opposed to the disclosure wherein the benzamide moiety is attached to one of the nitrogens which makes up the five membered ring of the imidazopyridine ring system.

SUMMARY OF THE INVENTION

The present invention relates to a novel class of compounds represented by the formula:

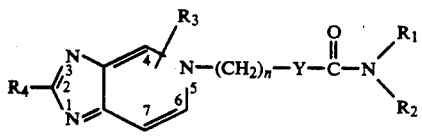

or a pharmaceutically acceptable acid addition salt thereof, wherein $R_1$ and $R_2$ are each independently selected from hydrogen; straight or branched chain alkyl of 1 to 15 carbon atoms; cycloalkyl having 3 to 8 carbon atoms; substituted cycloalkyl which can be substituted one or more by alkyl of 1 to 6 carbon atoms; bicycloalkyl having 3 to 8 carbon atoms in each ring; heterocyclicalkyl having 4 to 8 carbon atoms which can be optionally substituted by alkyl of 1 to 6 carbon atoms; heteroaromatic having 5 or 6 carbon atoms which can be optionally substituted by alkyl having 1 to 6 carbon atoms; phenyl; substituted phenyl which can be substituted one or more by a group independently selected from alkyl having 1 to 6 carbon atoms or halogen; straight or branched alkenyl having 3 to 15 carbon atoms with the proviso that the double bond of the alkenyl group cannot be adjacent to the nitrogen; cycloalkenyl having 5 to 8 carbon atoms with the proviso that the double bond cannot be adjacent to the nitrogen; and $R_1$ and $R_2$ cannot both be hydrogen;

Y is phenyl or phenyl substituted once or more than at one or more of the 2, 3, 5 or 6 positions of the phenyl ring by substituents independently selected from the group consisting of alkoxy having 1 to 6 carbon atoms; halogen wherein the halogen is selected from bromo, fluoro, or chloro; straight or branched chain alkyl having 1 to 6 carbon atoms; substituted straight or branched chain alkyl which can be substituted one or more by halogen; thioalkyl wherein the alkyl has 1 to 6 carbon atoms; alkoxyalkyl wherein the alkyl groups are each 1 to 6 carbon atoms; hydroxyalkyl wherein the alkyl has 1 to 6 carbon atoms; alkylthioalkyl wherein the alkyl groups are each 1 to 6 carbon atoms; cyano; mercaptoalkyl wherein the alkyl has 1 to 6 carbon atoms; hydroxy; amino; alkylamino wherein the alkyl group has 1 to 6 carbon atoms; and dialkylamino wherein the alkyl groups are each 1 to 6 carbon atoms;

n is an integer of 1 to 5;

$R_3$ is a group substituted at one or more of the 4, 6, or 7 positions of the pyridine ring said group being independently selected from hydrogen; alkyl having 1 to carbon atoms; halogen wherein the halogen is selected from bromo, fluoro or chloro; and alkoxy having 1 to 6 carbon atoms; and $R_4$ is hydrogen or alkyl having 1 to 6 carbon atoms;

The invention further relates to pharmaceutical compositions comprising a compound of formula I. Such compounds and compositions have potent and specific PAF antagonistic activities and are thereby useful in the treatment of various diseases or disorders mediated by PAF, for example inflammation, cardiovascular disorders, asthma, lung edema, and adult respiratory distress syndrome.

A preferred embodiment of the present invention are compounds of the formula:

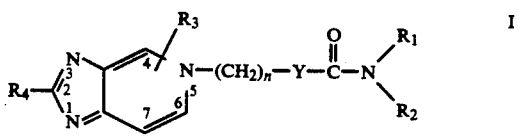

or a pharmaceutically acceptable acid addition salt thereof, wherein $R_1$ and $R_2$ are each independently selected from hydrogen; straight or branched chain alkyl having 1 to 15 carbon atoms; cycloalkyl having 3 to 8 carbon atoms; substituted cycloalkyl which can be substituted one or more by alkyl of 1 to 6 carbon atoms; bicycloalkyl having 3 to 8 carbon atoms in each ring; phenyl; substituted phenyl which can be substituted one or more by a group independently selected from alkyl having 1 to 6 carbon atoms and halogen; straight or branched alkenyl having 3 to 15 carbon atoms with the proviso that the double bond of the alkenyl group cannot be adjacent to the nitrogen; cycloalkenyl having 5 to 8 carbon atoms with the proviso that the double bond cannot be adjacent to the nitrogen; and $R_1$ and $R_2$ cannot both be hydrogen;

Y is phenyl or phenyl substituted once or more than at one or more of the 2, 3, 5 or 6 positions of the phenyl ring by substituents independently selected from the group consisting of alkoxy having 1 to 6 carbon atoms; halogen wherein the halogen is selected from bromo, fluoro, or chloro; straight or branched chain alkyl having 1 to 6 carbon atoms; substituted straight or branched chain alkyl which can be substituted one or more by halogen;

n is an integer of 1 to 5;

$R_3$ is a group substituted at one or more of the 4, 6, or 7 positions of the pyridine ring said group being independently selected from hydrogen; alkyl having 1 to 6 carbon atoms; halogen wherein the halogen is selected from bromo, fluoro or chloro; and alkoxy having 1 to 6 carbon atoms; and $R_4$ is hydrogen or alkyl of 1 to 6 carbon atoms.

A further embodiment of the present invention are compounds of the formula:

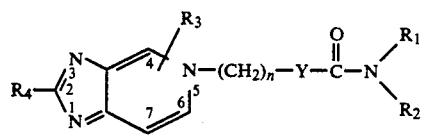

or a pharmaceutically acceptable acid addition salt thereof, wherein $R_1$ and $R_2$ are each independently selected from hydrogen; straight or branched chain alkyl having 1 to 15 carbon atoms; cycloalkyl having 3 to 8 carbon atoms; substituted cycloalkyl which can be substituted one or more by alkyl having 1 to 6 carbon atoms; phenyl; substituted phenyl which can be substituted one or more by the group independently selected from alkyl having to 6 carbon atoms and halogen; and $R_1$ and $R_2$ cannot both be hydrogen;

Y is phenyl or phenyl substituted once or more than at one or more of the 2, 3, 5 or 6 position of the phenyl ring by substituents independently selected from the group consisting of alkoxy having 1 to 6 carbon atoms; halogen wherein the halogen is selected from bromo, fluoro, or chloro; and straight or branched chain alkyl having 1 to 6 carbon atoms;

n is an integer of 1 to 5;

$R_3$ is a group substituted at one or more of the 4, 6, or 7 positions of the pyridine ring said group being independently selected from hydrogen and alkyl having 1 to 6 carbon atoms;

$R_4$ is hydrogen or alkyl having 1 to 6 carbon atoms.

As used herein the term "alkyl having 1 to 15 carbon atoms": refers to straight chain or branched chain hydrocarbon groups having from one to fifteen carbon atoms. Illustrative of such alkyl groups are methyl, ethyl, propyl isopropyl, butyl, isobutyl, pentyl, neopentyl, hexyl, isohexyl, octyl, decyl and the like.

As used herein the term "cycloalkyl having 3 to 8 carbon atoms" includes cycloalkyl groups having from three to eight carbons. Illustrative of such cycloalkyl group are cyclopropyl, cyclobutyl, cyclopentyl, cyclohexyl, cycloheptyl, cyclooctyl and the like.

As used herein the term halogen includes fluoro, chloro and bromo.

As used herein the term "alkenyl having 2 to 15 carbon atoms" refers to straight or branched unsaturated hydrocarbon groups having from 2 to 15 carbon atoms. Illustrative of such alkenyl groups are 2-propenyl, hexenyl, octenyl, decenyl and the like.

As used herein the term "alkoxy wherein the alkyl is 1 to 6 carbon atoms" refers to straight o branched chain ethers. Illustrative of such groups are methoxy, ethoxy, propoxy, butoxy, isopropoxy and the like.

The term "hydroxyalkyl" refers to straight or branched alkyl group having one to six atoms any one of which may be substituted with one or more hydroxyl group.

The term "thioalkyl" refers to straight or branched thio-containing radicals, respectively having alkyl portions of one to six attached.

The term "mercaptoalkyl" refers to a terminal mercapto group attached to an alkyl portion of one to six carbon atoms which can be straight or branched.

The term "heterocyclicalkyl" refers to a cyclic radicals having 5 to 8 carbon atoms wherein one or more of the carbons is replaced by nitrogen, sulfur or oxygen.

The term heteroaromatic refers to cyclic radicals having 5 or 6 ring carbon atoms which can be optionally substituted one or more times by alkyl of 1 to 6 carbon atoms with the understanding that the 5 membered carbon atom ring is replaced one or more times by nitrogen, sulfur or oxygen and when more than one hetero atom exists in the 5-membered ring one hetero atom must be nitrogen; the six membered carbon atom ring is replaced one or more times by nitrogen.

Included within the embodiments of the present invention are the tautomeric forms of the described compounds, isomeric forms including geometric isomers, enantimoers and diastereoisomers, and the pharmaceutically acceptable salts thereof.

The term "pharmaceutically acceptable acid addition salt" refers to a salt prepared by contacting a compound of formula (I) with an acid whose anion is generally considered suitable for human consumption. Examples of pharmacologically acceptable acid addition salts include the hydrochloride, hydrobromide, hydroiodide, sulfate, phosphate, acetate, propionate, lactate, maleate, malate, succinate, and tartrate salts. All of these salts may be prepared by conventional means by reacting, for example, the appropriate acid with the corresponding compound of Formula I.

The compounds of formula (I) may be prepared in accordance with the following procedures.

Imidazopyridine which is represented by the following formula

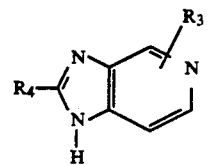

wherein $R_3$ and $R_4$ are defined as before is reacted with a haloalkylbenzamide which is represented by the following formula

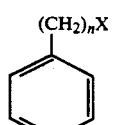

III

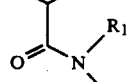

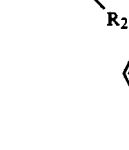

Preparation of Intermediates

Scheme A

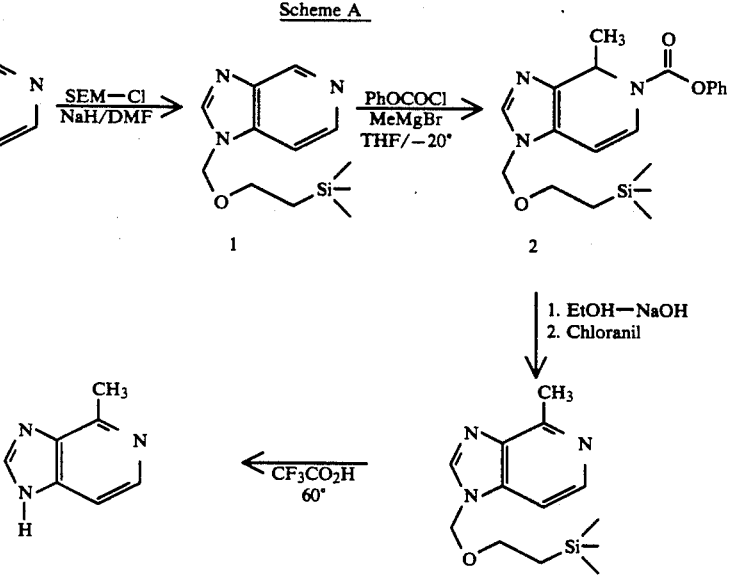

wherein $R_1$ and $R_2$ and n are defied as before and X is chloro, bromo, or methanesulfonyloxy to give the compounds of formula I. It is understood that the haloalkylbenzamide can also be substituted by halogen, alkyl of 1 to 6 carbon atoms; alkoxy wherein the alkyl is 1 to 6 carbon atoms; thioalkyl wherein the alkyl is 1 to 6 carbon atoms; alkoxy alkyl wherein the alkyl is 1 to 6 carbon atoms; hydroxyalkyl wherein the alkyl is 1 to 6 carbon atoms; alkylthioalkyl wherein the alkyl is 1 to 6 carbon atoms; cyano; mercaptoalkyl wherein the alkyl is 1 to 6 carbon atoms; hydroxy; amino; alkylamino wherein the alkyl group are each 1 to 6 carbon atoms and dialkylamino wherein the alkyl group are each 1 to 6 carbon atoms.

Preferred reaction conditions for the above-identified procedure include heating overnight at room temperature—90° C. a solution of haloalkylbenzamide and imidazopyridine in a solvent such as dimethylacetamide (approximately 0.1M in each). After heating overnight the reaction solvent is removed in vacuo and the residue diluted with water and basified with ammonium hydroxide. The aqueous solution is extracted with chloroform and the combined organic extracts are backwashed with saturated aqueous sodium chloride solution. The organic solution is dried over sodium sulfate or magnesium sulfate, the drying agent filtered and the filtrate concentrated in vacuo to give the crude product. Purification is effected by chromatography on silica gel using mixtures of chloroform, ethanol and ammonium hydroxide.

A preferred work up for the above-described procedure is to cool the reaction solution which had been heated overnight to room temperature and remove the solvent under reduced pressure at $<45°$ C. The residue obtained is triturated with excess of dry ether and filtered. The crude product is purified by chromatography.

The imidazo [4,5-c]pyridine wherein $R_3$ is 4-methyl is prepared according to the scheme above starting with the imidazopyridine of Formula II. Position 1 of this compound is protected by reaction with a 2-(trialkylsilyl) ethoxy methyl chloride and a base such as sodium hydride or potassium hydride in a polar aprotic solvent such as dimethylformamide. This reaction is carried out at room temperature. A specific example of such a protecting reagent is 2-(trimethylsilyl)ethoxymethyl chloride. The protected imidazopyridine is reacted with phenyl chloroformate and methylmagnesium bromide in an ether solvent such as tetrahydrofuran at about $-20°$ C. The methylated product bearing phenoxycarbonyl at position 5 is treated with a base, such as alcoholic sodium hydroxide, at reflux for 24 h. The product is oxidized with, for example, chloranil, and the 2-(trimethylsilyl)ethoxymethyl group is removed by treatment with a suitable acid. An example of such an acid would be trifluoroacetic acid. Preparation of the unsubstituted imidazo [4,5-c] pyridine is described in U.S. Pat. No. 4,804,658.

The haloalkyl benzamides are prepared according to the following reaction scheme

Scheme B

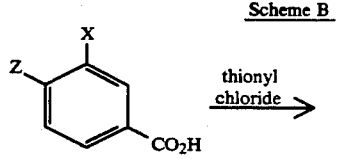

-continued
Scheme B

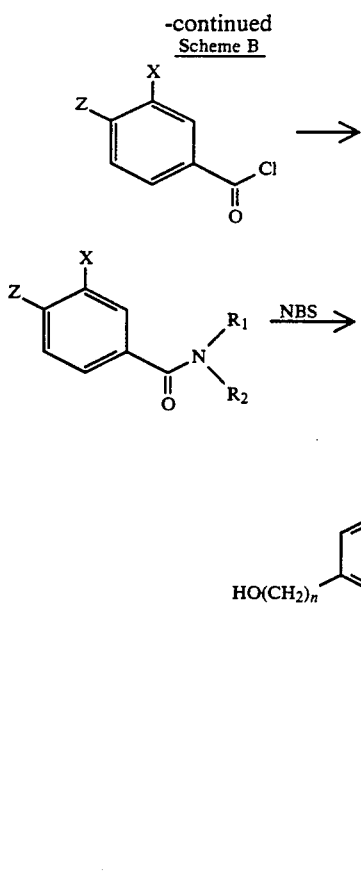

wherein $R_1$ and $R_2$ are defined as before; Z is $CH_2Br$ or H; X is fluoro, OMe or methyl Thus according to the above scheme the acid chlorides are prepared from the corresponding carboxylic acids by refluxing in thionyl chloride (2 molar excess) for two hours. Excess thionyl chloride is removed by azeotrope with toluene. The residual acid chloride is dissolved in THF and cooled to $-10°$ C. A solution of two molar equivalents of the secondary amine in the THF is added dropwise with stirring. When addition is completed, the reaction is allowed to warm to room temperature and stirred for 1-2 hours. The reaction is quenched with IN HCL, diluted with $H_2O$ and extracted three times with ethyl acetate. The combined organic layers are washed with saturated aqueous sodium bicarbonate solution, with water and with saturated aqueous sodium chloride and dried over sodium sulfate. The drying agent is filtered and the filtrate concentrated in vacuo to give a crude product that was chromatographed on silica gel using mixtures of ethyl acetate and hexane to give the purified amide.

When Z is $CH_2Br$ and X is H, the above description is sufficient for the preparation of the compounds of Formula III. When Z is $CH_3$, and X is OMe or F, or when Z is H and X is $CH_3$ then compound of Formula VI must be treated with a halogenating agent such as N-bromo succinimide.

A stirred mixture of the purified amide and NBS (1:1 molar ratio) in carbon tetrachloride is irradiated with a sun lamp for 1-3 hours. A white precipitate is filtered and washed with a minimum amount of $CHCl_3$. The filtrate is washed with water and the aqueous layer, after basification with ammonium hydroxide, is extracted three times with chloroform. All organic layers are combined, washed three times with saturated aqueous sodium chloride solution and dried over sodium sulfate.

The drying agent is filtered and the filtrate concentrated in vacuo to give a crude product that is chromatographed on silica gel using mixtures of ethyl acetate and hexane to give the purified bromomethyl compound.

Scheme C

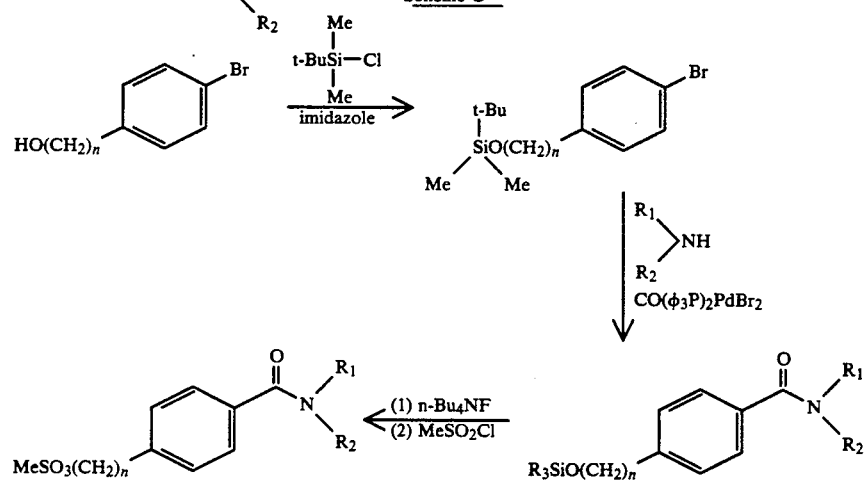

The benzamides wherein n is 2 or 3 can be prepared according to the scheme C starting with he appropriate hydroxyalkyl bromobenzene. The hydroxyl group is protected as a trialkylsilyl ether by reaction with a trialkylsilyl chloride and imidazole in a suitable solvent such as dimethylformamide. An example of such a protecting group would be the t-butyldimethylsilyl ether. The crude silyl ether is purified by chromatography on silica gel using mixtures of ethyl acetate and hexane. The aryl bromide is converted to the carboxamide according to the procedure of Schoenberg et al. [J. Org. Chem., 39, 3327(1974)]. Thus, the aryl bromide is reacted with carbon monoxide in the secondary amine as solvent using bistriphenylphosphine palladium(II) dibromide as catalyst at about 100° C. for 8-26 h. in a pressure vessel. The reaction vessel is vented, the reaction mixture triturated with ethyl ether and the washings filtered. The filtrate is washed with 10% aqueous HCl, water and brine. After drying over a suitable drying agent, such as magnesium sulfate, and filtering, the filtrate is concentrated and the residue chromatographed on silica gel using mixtures of ethyl acetate and hexane as eluent to give pure product. The silyl ether is removed by reaction with tetra-n-butylammonium fluoride and the alcohol is converted to a sulfonate ester by reaction with an alkyl or arylsulfonyl chloride. An example of such a sulfonate would be the methanesulfonate.

The secondary amines may be prepared by any number of methods known to those skilled in the art. See references Emerson, W. S. Org. Reactions 4, 174 1948)
J. B. Cambell, L. B. Lavaginino in "Catalysis in Organic Syntheses" (Jones W. H., ed.) p. 43, Academic Press, New York, 1980.
Preparation of 4-Methyl-7-methoxy-imidazopyridine
The above compound can be prepared by the following scheme:
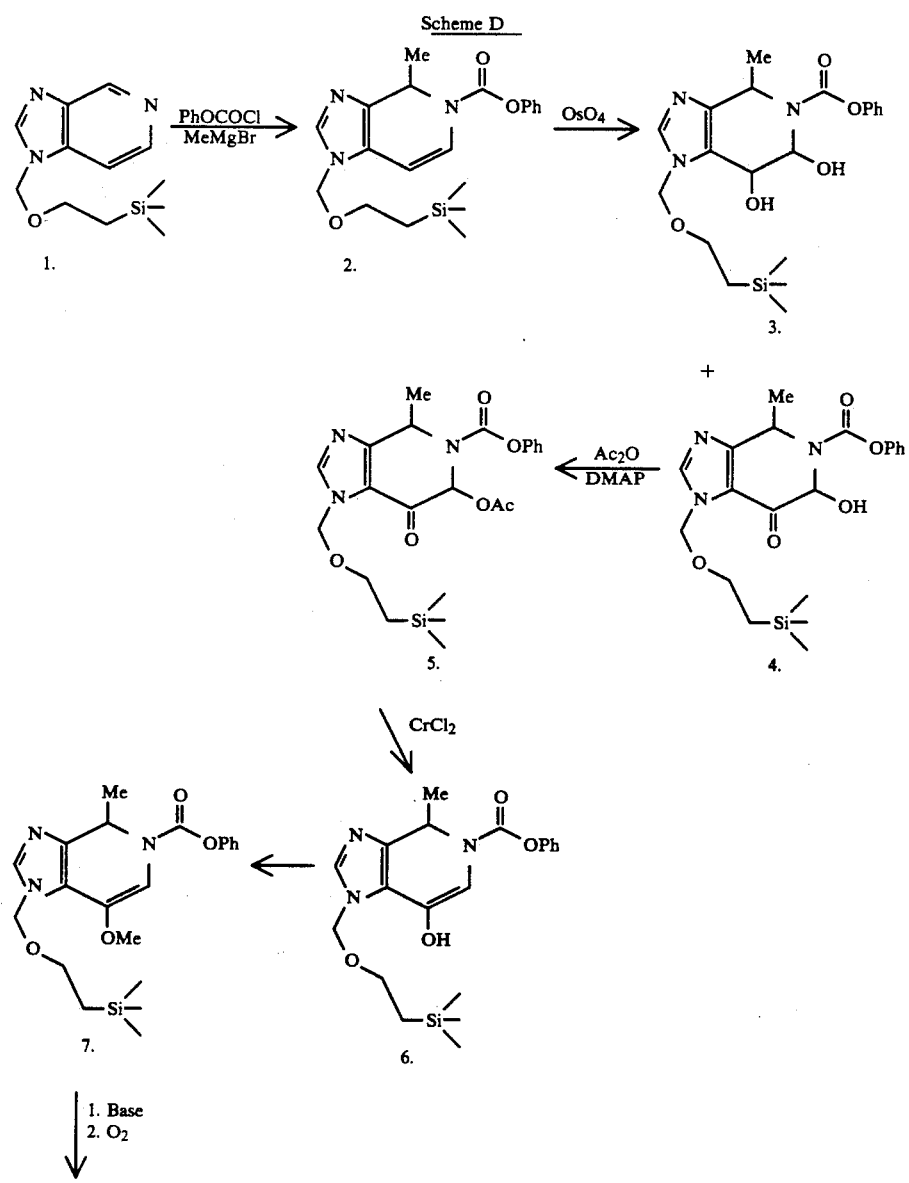

Scheme D

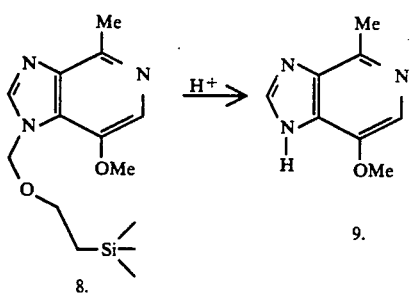

Thus the addition product 2 which is isolated on reacting 1 with phenyl chloroformate and methyl magnesium bromide is treated with osmium tetroxide in aqueous acetone containing N-methylmorpholine-N-oxide at room temperature for 24 hours to give the diol 3 and the hydroxyketone 4. The hydroxyketone 4 is acetylated (acetic anhydride, DMAP methylene chloride, room temperature, 24 hrs) and treated with $CrCl_2$ in acetone to give the deacetoxylated product 6. Product 6 is treated with NaH in DMF and then with iodomethane to give the methyl ether 7. Clevage of carbamate and oxidation gives the N-1 protected 4-methyl-7-methoxy imidazopyridine product 8. Deprotection of product 8 gives the 4-methyl-7-methoxyimidazopyridine.

Preparation of 2-Methoxy-4-bromomethyl-5-bromobenz(N-cyclopentyl,N-2-methylcyclohexyl)amide

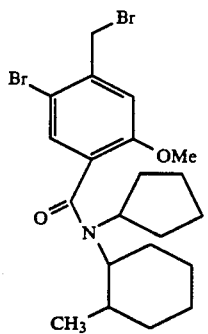

The above compound is prepared from 2-methoxy-4-methylbenz (N-cyclopentyl,N-2-methylcyclohexyl)amide and N-bromo succinimide in carbon tetrachloride by irradiation with a sun lamp for 5 hours.

Preparation of 2,6-Dimethoxy-3 bromo-4-bromomethylbenz (N-cyclohexyl,N-cyclopentyl)amide

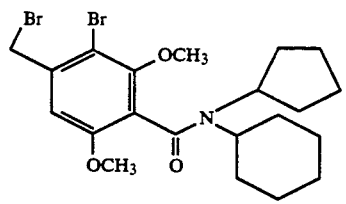

The above compound is prepared from 2,6-dimethoxy-4-methyl benzoic acid described by I. W. Mathison, R. C. Gueldner, D. M. Carroll, J. Pharma Sci 57 1820, (1968). The substituted benzoic acid is converted to the corresponding amide by first converting said compound to the acid chloride (using thionyl chloride) followed by condensation with N-cyclohexyl,N-cyclopentylamine. Irradiation of 2,6-dimethoxy-4-methyl-benz(N-cyclohexyl, N-cyclopentyl)amide following the procedure described for the preparation 2-methoxy-4-bromomethyl-5-bromobenz-N-cyclopentyl,N-2 methylcyclohexyl)amide gives two products 2,6-dimethoxy-3-bromo-4-methylbenz-(N-cyclohexyl, N-cyclopentyl)amide and 2,6-dimethoxy-3-bromo-4-bromomethylbenz(N-cyclohexyl,N-cyclopentyl)amide.

Scheme E

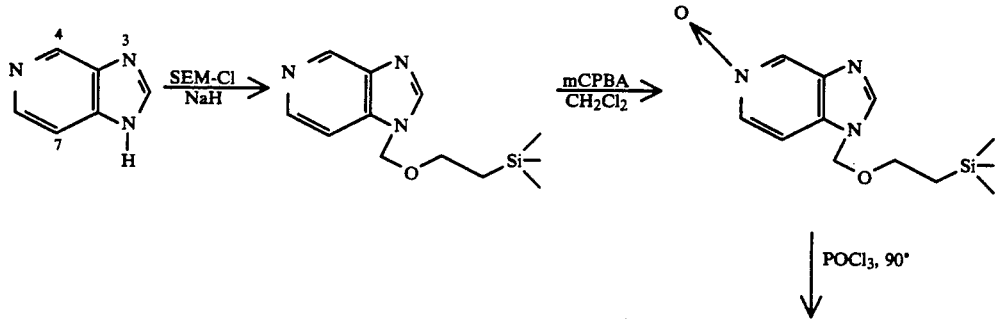

-continued
Scheme E

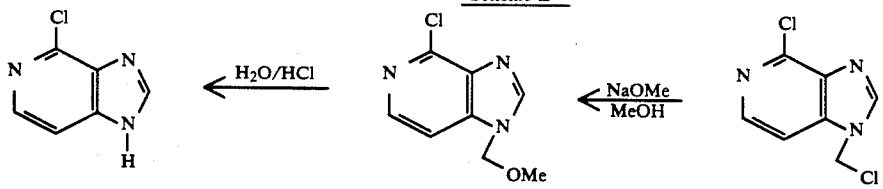

The imidazo[4,5-c]pyridine wherein R₃ is 4-chloro is prepared according to Scheme E starting with the imidazopyridine of Formula II. Position 1 of this compound is protected by reaction with a 2-trialkylsilyl) ethoxy methyl chloride and a base such as sodium hydride or potassium hydride in a polar aprotic solvent such as dimethylformamide. The reaction is carried out at room temperature. The protected imidazopyridine is reacted with m-chloroperbenzoic acid in methylene chloride at room temperature to give the pyridine N-oxide product. The N-oxide product is heated in POCl₃ at 90° C. to give 4-chloro-1-chloromethyl imidazopyridine. Treatment of this compound with sodium methoxide in methanol gives the 4-chloro-1-methoxy ethyl imidazopyridine. Reacting this compound with water/acid with heating gives the 4-chloro-imidazo[4,5-c] pyridine.

Preparation of Alkoxyalkyls

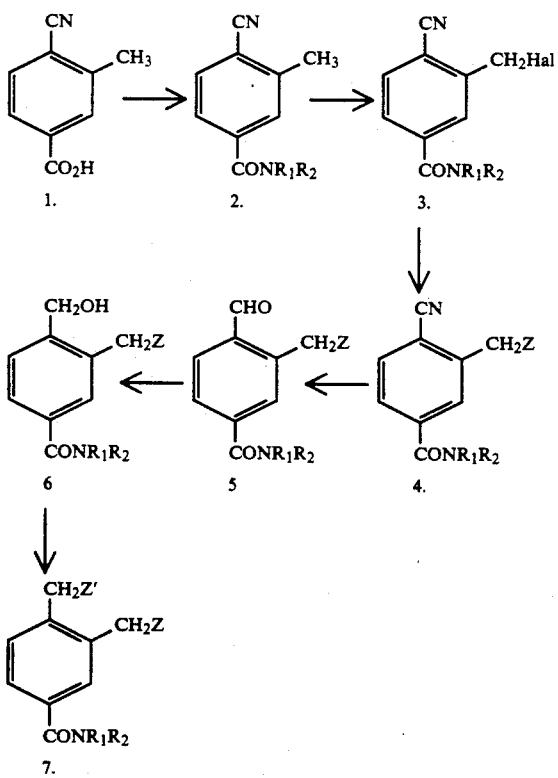

wherein R₁ and R₂ are defined as before; "Hal" is halogen; Z is alkoxy, thioalkyl, mercapto, hydroxy, halo, amino, alkyl and dialkylamino; and Z' chloro, bromo, methanesulfonyloxy or p-toluenesulfonyloxy.

When Y is substituted with alkoxyalkyl, such substitution may be carried out by methods known to those skilled in the art. Such a method might, for example, employ the substituted benzoic acid 1 (F. Fichter, G. Shetty, Helv. Chim. Acts, 20, 563 (1937)) as starting material. This is coverted to the amide 2 by first converting acid 1 to the acid chloride by contact with agents such as oxalyl chloride or thionyl chloride and then treating the acid chloride with the desired amine. Amide 2 is converted to halide 3 by treatment with a halogenating agent such as N-bromosuccinimide. Halide 3 is versatile and in addition to serving as an intermediate to alkoxyalkyl compounds, is also an intermediate to alkylthioalkyl, hydroxyalkyl, mercaptoalkyl and alkylaminoalkyl compounds by treatment with the appropriate Z derivative. When halogen is displaced with a metal alkoxide, such as sodium methoxide, the methoxymethyl derivative (4, Z is OMe) is obtained. Conversion of 4 (Z is OMe) to aldehyde 5 (Z is OMe) is effected by controlled reduction with a reducing agent such as diisobutylaluminum hydride, followed by acid hydrolysis. Reduction of aldehyde 5 to alcohol 6 is effected by a second reduction with another reducing agent such as sodium borohydride or lithium tri-t-butoxyaluminum hydride. Alcohol 6 is converted to a derivative suitable for nucleophilic displacement such as 7 where Z' is a leaving group such as halide or aryl or alkyl sulfonate. Such conversion is effected by treatment of 6 with, for example, p-toluenesulfonyl chloride, methanesulfonyl chloride, or thionyl chloride.

Compounds where Y of formula I is substituted with hydroxy can be made from the corresponding methoxy substituted compounds by treatment with a demethylating reagent such as lithium ethyl mercaptide in a dipolar, aprotic solvent such as dimethylformamide at temperatures ranging from room temperature to 200° C.

This invention also relates to a method of treatment for patients (or mammalian animals raised in the dairy, meat, or fur industries or as pets) suffering from disorders or diseases which can be attributed to PAF as previously described, and more specifically, a method of treatment involving the administration of compound (I) as the active ingredient.

Accordingly, compound (I) can be used among other things to reduce inflammation, to correct respiratory, cardiovascular, and intravascular alterations or disorders, and to regulate the activation or coagulation of platelets, the pathogenesis of immune complex deposition and smooth muscle contractions.

For the treatment of inflammation, cardiovascular disorder, asthma, or other diseases mediated by PAF, compound (I) may be administered orally, topically, parenterally, or by inhalation spray or rectally in dosage unit formulations containing conventional non-toxic pharmaceutically acceptable carriers, adjuvants and vehicles. The term parenteral as used herein includes subcutaneous, intravenous, intramuscular, intrasternal, infusion techniques or intraperitoneally.

The compounds of the present invention may be administered by any suitable route, preferably in the form of a pharmaceutical composition adapted to such a route, and in a dose effective for the treatment intended. Therapeutically effective doses of the compounds of the present invention required to prevent or arrest the progress of the medical condition are readily ascertained by one of ordinary skill in the art.

Accordingly, the invention provides a class of novel pharmaceutical compositions comprising one or more compounds of the present invention in association with one or more non-toxic, pharmaceutically acceptable carriers and/or diluents and/or adjuvants (collectively referred to herein as "carrier" materials) and if desired other active ingredients.

The dosage regimen for treating a condition with the compounds and/or compositions of this invention is selected in accordance with a variety of factors, including the type, age, weight, sex and medical condition of the patient; the severity of the infection; the route of administration; and the particular compound employed and thus may vary widely.

Dosage levels of the order from about 0.01 mg to about 100 mg per kilogram of body weight per day are useful in the treatment of the above-indicated conditions (from about 0.5 mg to about 5 gs. per patient per day). Preferably, from about 0.01 mg to about 50 mg per kilogram of body weight per daily dosage produces highly effective results (about 0.5 mg to about 2.5 gm per patient per day).

For oral administration, the pharmaceutical composition may be in the form of, for example, a tablet, capsule, suspension or liquid. The pharmaceutical composition is preferably made in the form of a dosage unit contained in a particular amount of the active ingredient. Examples of such dosage units are tablets or capsules which may be taken singly or multiply. These may with advantage contain an amount of active ingredient from about 0.5 to 250 mg preferably from about 0.5 to 150 mg. A suitable daily dose for a mammal may vary widely depending on the condition of the patient and other factors. However, a dose of from about 0.01 to 100 mg/kg body weight, particularly from about 0.01 to 75 mg/kg body weight may be appropriate.

The active ingredient may also be administered by injection as a composition wherein, for example, saline, dextrose or water may be used as a suitable carrier. A suitable daily dose is from about 0.01 to 100 mg/kg body weight injected per day in single or multiple doses or continuous infusion depending on the disease being treated. A preferred daily dose would be from about 0.01 to 50 mg/kg body weight.

For administration, the compounds of this invention are ordinarily combined with one or more adjuvants appropriate to the indicated route of administration. The compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulphuric acids, gelatin, acacia, sodium alginate, polyvinylpyrrolidone, and/or polyvinyl alcohol, and thus tableted or encapsulated for convenient administration. Alternatively, the compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

The pharmaceutical compositions may be made up in a solid form such as granules, powders or suppositories or in a liquid form such as solutions, suspensions or emulsions. The pharmaceutical compositions may be subjected to conventional pharmaceutical operations such as sterilization and/or may contain conventional pharmaceutical adjuvants such as preservatives, stabilizers, wetting agents, emulsifiers, buffers, etc.

The amount of active ingredient that may be combined with the carrier materials to produce a single dosage form which may be taken singly or multiply will vary depending upon the host treated and the particular mode of administration. For example, a formulation intended for the oral administration of humans may contain from 0.5 mg to 250 mg of active agent compounded with an appropriate and convenient amount of carrier material which may vary from about 5 to 95 percent of the total composition. Dosage unit forms will generally contain between from about 0.5 mg to about 150 mg of active ingredient.

The following Examples are intended to further illustrate the present invention and not to limit the invention in spirit or scope. In the Examples, all parts are parts by weight unless otherwise expressly set forth.

EXAMPLE 1

Preparation of
5-[4-(N-methyl-N-cyclohexylcarboxamido)benzyl-]imidazo[4,5-c]pyridine

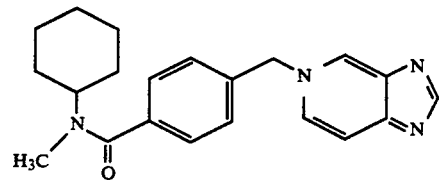

To a stirred solution of imidazopyridine (5.86 g, 49.2 mmol) in DMF (125 ml) under a nitrogen atmosphere was added washed, dried sodium hydride (prepared from 3.54 g of 50% dispersion in oil by washing four times with 50–75 ml portions of hexane). After stirring for 1 hr at room temperature, the evolution of hydrogen gas had ceased and the reaction was cooled to −10° C. N-Methyl-N-cyclohexyl-a-bromo-p-toluyl amide (16.9 g, 54.5 mmol) was added. The reaction was stirred at 0° for 45 min. and at room temperature for 3 hrs.

DMF was removed in vacuo and the residue was diluted with $H_2O$ (200 ml) and the resulting solution was saturated with sodium chloride. The aqueous solution was extracted four times with ethyl acetate (100 ml portions) and the combined organic layers were washed three times with saturated aqueous sodium chloride solution (150 ml portions). After drying over sodium sulfate, the organic solution was filtered and concentrated in vacuo to give 13.38 g of crude product as a brown gum. This material was chromatographed on silica gel using ethanol/chloroform/ammonium hydroxide (20/79/1) to give 13.38 g of compound as an orange oil that crystallized on treatment with ethyl acetate. Recrystallization from ethyl acetate yielded 1.06 g. The resulting product had the following properties:

Analysis Calcd for $C_{21}H_{24}N_4O \cdot 1/4H_2O$: C, 71.46; H, 7.00; N, 15.88. Found: C, 71.14; H, 7.18; N, 15.78. m.p. 115°–17° C.

EXAMPLE 2

Preparation of 5-[4-(N,methyl-N-cyclohexylcarboxamido)-2-fluorobenzyl]imidazo[4,5-c]pyridine

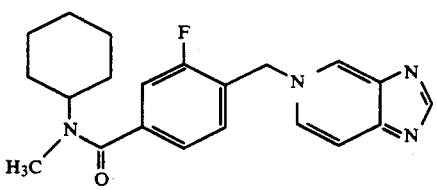

A solution of N-methyl, N-cyclohexyl 3-fluoro 4-bromomethyl benzamide (1.2 g 2.66 mm) and imidazopyridine (0.48 g 4.0 mm) in dimethylacetamide (25 ml) was heated overnight at 70°–80° C. with stirring under $N_2$. Reaction solvent was removed in vacuo and the residue diluted with water and basified with ammonium hydroxide. The aqueous solution was extracted four times with chloroform and the combined organic extracts were backwashed three times with saturated aqueous sodium chloride solution. The organic solution was dried over magnesium sulfate, the drying agent was filtered and the filtrate concentrated in vacuo to give 0.88 g of the crude compound. Purification of the compound was effected by chromatography on silica using mixtures of chloroform, ethanol and ammonium hydroxide. The resulting product had the following properties: Analysis calcd for $C_{21}H_{23}FN_4O$ 0.8 $H_2O$: C, 66.22; H, 6.51; N, 14.71; F, 4.99. Found: C, 66.03; H, 6.44; N, 14.65; F, 4.91. m.p. 154°–158° C.

In the same manner as described in Example 2 the compounds of the Examples 3 to 11 described in Tables A & B were prepared.

TABLE A

| Example | $R_1$ | $R_2$ | X | n | $R_3$ | $R_4$ | M pt (°C.) | Analysis Calcd. | Found | Molecular Formula |
|---|---|---|---|---|---|---|---|---|---|---|
| 3 | cyclopentylmethyl | cyclopentyl | $OCH_3$ | 1 | H | H | 217–19 | C 71.12 / H 7.26 / N 13.28 | 70.83 / 7.33 / 13.06 | $C_{25}H_{30}N_4$ |
| 4 | cyclohexylmethyl | cyclopentyl | $OCH_3$ | 1 | H | H | 197–99 | C 71.01 / H 7.52 / N 12.74 | 70.87 / 7.49 / 12.70 | $C_{26}H_{32}N_4O$ 0.4$H_2O$ |
| 5 | cyclohexylmethyl | isopropyl | $OCH_3$ | 1 | H | H | 192–95 | C 70.90 / H 7.44 / N 13.78 | 70.75 / 7.47 / 13.71 | $C_{24}H_{30}N_4O$ |
| 6 | cyclohexylmethyl | $CH_3$ | $OCH_3$ | 1 | H | H | 206–08 | C 69.15 / H 6.86 / N 14.67 | 68.78 / 6.88 / 14.57 | $C_{22}H_{26}N_4O$ 0.2$H_2O$ |
| 7 | cyclohexylmethyl | cyclopentylmethyl | F | 1 | H | H | 205–08 | C 71.14 / H 6.95 / N 13.33 / F 4.52 | 71.11 / 7.11 / 13.16 / 4.30 | $C_{25}H_{29}FN_4O$ |
| 8 | cyclohexylmethyl | isopropyl | F | 1 | H | H | 178–82 | C 68.46 / H 6.79 / N 13.89 / F 4.71 | 68.46 / 6.71 / 13.45 / 4.38 | $C_{23}H_{27}FN_4$ 0.5$H_2O$ |

TABLE A-continued

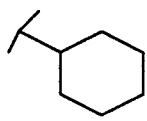

| Example | R₁ | R₂ | X | n | R₃ | R₄ | M pt (°C.) | | Analysis Calcd. | Found | Molecular Formula |
|---|---|---|---|---|---|---|---|---|---|---|---|
| 9 | cyclohexylmethyl | CH₃ | F | 1 | H | H | 154–8 | C | 66.22 | 66.03 | $C_{21}H_{23}N_4F$ |
| | | | | | | | | H | 6.51 | 6.44 | |
| | | | | | | | | N | 14.71 | 14.65 | 0.8H₂O |
| | | | | | | | | F | 4.99 | 4.91 | |

TABLE B

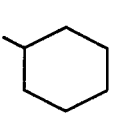

| Example | R₁ | R₂ | M pt (°C.) | | Analysis Calcd. | Found | Molecular Formula |
|---|---|---|---|---|---|---|---|
| 10 | cyclohexyl | —CH₃ | 167–69 | C | 72.38 | 72.26 | $C_{21}H_{24}N_4O$ |
| | | | | H | 6.94 | 7.10 | |
| | | | | N | 16.08 | 16.01 | |
| 11 | cyclohexyl | isobutyl | 209–12 | C | 73.37 | 72.97 | $C_{23}H_{28}N_4O$ |
| | | | | H | 7.50 | 7.63 | |
| | | | | N | 14.88 | 14.61 | |

EXAMPLE 12

Preparation of
5-[(4-(N,N-dicyclohexylcarboxamido)benzyl-]imidazo[4,5-c]pyridine

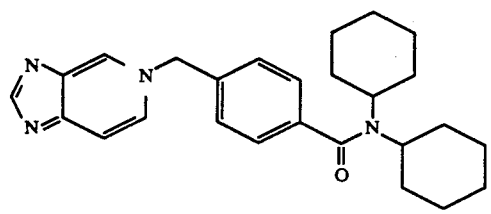

To a stirred solution of imidazopyridine (750 mg, 6.3 mmol) in N,N-dimethylacetamide, 4-bromomethyl-N,N-dicyclohexyl benzamide (2.6 g, 6.88 mmol) was added. The reaction mixture was stirred under argon at 80°–85° C. After 24h, the reaction flask was cooled to room temperature and the solvent removed under reduced pressure at <45° C. The residue obtained was triturated with ether (2×70 mL) and filtered. The crude product (2.7 g) was chromatographed (silica gel, CH₂Cl₂—MeOH—NH₄OH 80-20-1) to give pure product (1.47 g, 62%) which was recrystallized from EtOAc-CH₃CN. The resulting product had the following properties: mp 233°–35° C.; Analysis calcd. for $C_{26}H_{32}N_4O$. 0.3H₂O: C, 74.0: H, 7.73: N, 13.28. Found C, 73.93; H, 7.90; N, 13.09. In the same manner as described in Example 12 the compounds of the Examples 13 to 38 described in Table C were prepared.

TABLE C

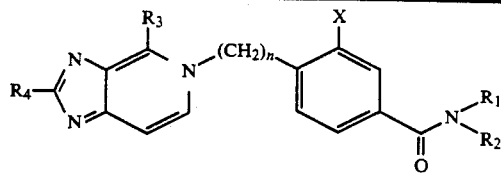

| Example | R₁ | R₂ | X | n | R₃ | R₄ | M pt (°C.) | | Analysis Calcd. | Found | Molecular Formula |
|---|---|---|---|---|---|---|---|---|---|---|---|
| 13 | cyclohexylmethyl | CH₃ | H | 1 | H | H | 115–17 | C H N | 71.46 7.00 15.88 | 71.14 7.18 15.78 | $C_{21}H_{24}N_4O$ 0.25$H_2O$ |
| 14 | -(CH₂)₇CH₃ | H | H | 1 | H | H | 113–15 | C H N | 72.52 7.69 15.38 | 72.26 7.72 15.28 | $C_{22}H_{28}N_4O$ |
| 15 | -(CH₂)₉CH₃ | H | H | 1 | H | H | 141–45 | C H N | 73.46 8.16 14.28 | 73.35 8.32 14.26 | $C_{24}H_{32}N_4O$ |
| 16 | cyclohexylmethyl | isobutyl | H | 1 | H | H | 209–10 | C H N | 72.70 7.48 14.75 | 72.92 7.60 14.82 | $C_{23}H_{28}N_4O$ 0.2$H_2O$ |
| 17 | cyclohexylmethyl | sec-butyl | H | 1 | H | H | 210–11 | C H N | 73.80 7.69 14.35 | 73.40 7.78 14.25 | $C_{24}H_{30}N_4O$ |
| 18 | -(CH₂)₁₁CH₃ | H | H | 1 | H | H | 150–2 | C H N | 74.28 8.57 13.33 | 74.10 8.75 13.36 | $C_{26}H_{36}N_4O$ |
| 19 | decalinyl | H | H | 1 | H | H | 113–28 | C H N | 73.31 7.52 13.68 | 73.41 7.79 13.38 | $C_{25}H_{30}N_4O$ 0.4$H_2O$ |
| 20 | neopentyl-t-butyl | H | H | 1 | H | H | 221–2 | C H N | 72.52 7.69 15.38 | 72.33 7.82 15.28 | $C_{22}H_{28}N_4O$ |
| 21 | cyclohexylmethyl | CH₃ | H | 2 | H | H | 223–5 | C H N | 71.15 7.27 15.09 | 70.79 7.48 14.81 | $C_{22}H_{26}N_4O$ 0.5$H_2O$ |
| 22 | cyclohexylmethyl | CH₃ | H | 3 | H | H | | C H N | 70.86 7.57 14.36 | 70.82 7.64 14.23 | $C_{23}H_{28}N_4O$ 0.75$H_2O$ |
| 23 | cyclopentylmethyl | cyclopentylmethyl | H | 1 | H | CH₃ | 197–98 | C H N | 74.62 7.46 13.93 | 74.24 7.50 13.80 | $C_{25}H_{30}N_4O$ |
| 24 | cyclopentyl | cyclopentyl | H | 1 | CH₃ | H | 225–8 | C H N | 72.31 7.48 13.18 | 72.36 7.57 13.50 | $C_{25}H_{30}N_4O$ 0.7$H_2O$ |

TABLE C-continued

Structure: R4-(imidazopyridine with R3)-N-(CH2)n-(phenyl with X)-C(=O)-N(R1)(R2)

| Example | R1 | R2 | X | n | R3 | R4 | M pt (°C) | Analysis Calcd. | Analysis Found | Molecular Formula |
|---|---|---|---|---|---|---|---|---|---|---|
| 25 | cyclohexyl | cyclobutylmethyl | H | 1 | H | H | 190–3 | C 74.22 H 7.21 N 14.43 | 73.98 7.27 14.33 | C₂₄H₂₈N₄O |
| 26 | cyclohexylmethyl | cyclopentylmethyl | H | 1 | H | H | 222–23 | C 74.62 H 7.46 N 13.93 | 74.21 7.45 14.26 | C₂₅H₃₀N₄O |
| 27 | cyclohexylmethyl | cyclohexylmethyl | H | 1 | H | H | 233–35 | C 74.0 H 7.73 N 13.28 | 73.93 7.90 13.07 | C₂₆H₃₂N₄O · 0.5H₂O |
| 28 | cyclohexylmethyl | tert-butylmethyl | H | 1 | H | H | 197–98 | C 73.84 H 7.69 N 14.35 | 73.86 7.87 14.35 | C₂₄H₃₀N₄O |
| 29 | benzyl | cyclopentylmethyl | H | 1 | H | H | 213–14 | C 75.73 H 6.10 N 14.13 | 75.66 6.18 14.08 | C₂₅H₂₄N₄O |
| 30 | (3-methylcyclohexyl)methyl | cyclopentylmethyl | H | 1 | H | H | 187–89 | C 74.94 H 7.74 N 13.44 | 74.58 7.84 13.32 | C₂₆H₃₂N₄O |
| 31 | (4-methylcyclohexyl)methyl | cyclopentylmethyl | H | 1 | H | H | 211–12 | C 74.94 H 7.74 N 13.44 | 74.85 7.84 13.39 | C₂₆H₃₂N₄O |
| 32 | cyclohexylmethyl | isobutyl | H | 1 | H | H | 198–200 | C 73.84 H 7.69 N 14.35 | 73.20 7.70 14.74 | C₂₄H₃₀N₄O |
| 33 | cyclohexylmethyl | 2,2-dimethylpropyl | H | 1 | H | H | 211–13 | C 73.60 H 7.85 N 13.73 | 73.72 7.92 13.72 | C₂₅H₃₂N₄O · 0.2H₂O |

TABLE C-continued

| Example | R₁ | R₂ | X | n | R₃ | R₄ | M pt (°C.) | Analysis Calcd. | Found | Molecular Formula |
|---|---|---|---|---|---|---|---|---|---|---|
| 34 | cyclohexylmethyl | cyclopropylmethyl | H | 1 | H | H | 88–90 | C 72.06<br>H 7.04<br>N 14.62 | 72.25<br>7.16<br>14.48 | $C_{23}H_{26}N_4O$<br>$0.5H_2O$ |
| 35 | isopropyl | isopropyl | H | 1 | H | H | 224–5 | C 71.42<br>H 7.14<br>N 16.66 | 71.30<br>7.29<br>16.71 | $C_{20}H_{24}N_4O$ |
| 36 | cyclopentylmethyl | cyclopentylmethyl | H | 1 | H | H | 228–30 | C 74.22<br>H 7.21<br>N 14.43 | 74.04<br>7.29<br>14.28 | $C_{24}H_{28}N_4O$ |
| 37 | cyclohexylmethyl | H | H | 1 | H | H | 219–21 | C 70.33<br>H 6.68<br>N 16.41 | 70.34<br>6.87<br>16.28 | $C_{20}H_{22}N_4O$<br>$0.4H_2O$ |
| 38 | cyclohexylmethyl | —CH₂CH₃ | H | 1 | H | H | 156–8 | C 71.85<br>H 7.24<br>N 15.24 | 71.85<br>7.24<br>15.19 | $C_{22}H_{26}N_4O$<br>$0.3H_2O$ |

EXAMPLE 39

Preparation of
5-[4{-(N-cyclopentyl,N-3,5-dimethylcyclohexyl) carboxamido}benzyl]imidazo[4,5-c]pyridine

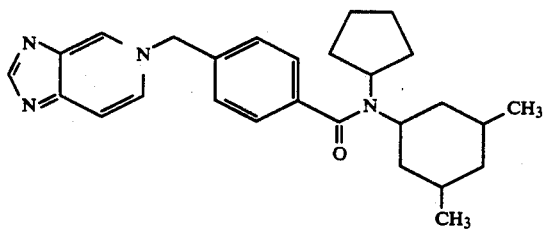

To a stirred solution of imidazopyridine (400 mg, 3.4 mmol) in N,N-dimethylacetamide (30 ml), 4-bromomethyl-N-cyclopentyl, N-3,5-dimethylcyclohexyl benzamide (1.4 g 3.57 mmol) was added. The reaction mixture was stirred under argon at 80°–85° C. After 40h, the reaction flask was cooled to room temperature and the solvent removed under reduced pressure at <45° C. The residue obtained was triturated with ether (2×70 ml) and filtered. The crude (1.8 g) was chromatographed (silica gel, CH₂Cl₂—MeOH—NH₄OH 90-10-1) to give pure product (1.05 g, 72%) which was recrystallized from EtOAc-CH₃CN. The resulting product had the following properties: mp 214°–16° C. Anal calcd. for $C_{27}H_{34}N_4O$: C, 75.30; H, 7.9; N, 13.02. Found C, 74.92; H, 8.07; N, 12.97.

In the same manner as described in Example 39 the compounds of the Examples 40 to 55 described in Table D were prepared.

TABLE D

*[Structure: imidazo-pyridine linked via N-CH2 to a benzamide with substituents R3, R4, R5, R6 and amide N-R1, R2]*

| Example | R1 | R2 | R3 | R4 | R5 | R6 | M pt (°C.) | Analysis Calcd. | Found | Molecular Formula |
|---|---|---|---|---|---|---|---|---|---|---|
| 40 | cyclopentyl-CH2 | 3-methylcyclopentyl-CH2 | H | H | H | H | 204–6 | C 74.62<br>H 7.46<br>N 13.93 | 74.12<br>7.56<br>13.90 | $C_{25}H_{30}N_4O$ |
| 41 | isopropyl | 3-methylcyclopentyl-CH2 | H | H | H | H | 229–31 | C 73.40<br>H 7.45<br>N 14.89 | 73.13<br>7.64<br>14.85 | $C_{23}H_{28}N_4O$ |
| 42 | cyclopentyl-CH2 | 3,5-dimethylcyclohexyl-CH2 | H | H | H | H | 214–16 | C 75.30<br>H 7.90<br>N 13.02 | 74.92<br>8.07<br>12.97 | $C_{27}H_{34}N_4O$ |
| 43 | cyclopentyl-CH2 | 2-methylcyclohexyl-CH2 | H | H | H | H | 223–5 | C 74.96<br>H 7.74<br>N 13.45 | 74.65<br>7.79<br>13.35 | $C_{26}H_{32}N_4O$ |
| 44 | cyclopentyl-CH2 | norbornyl | H | H | H | H | 182–5 | C 75.00<br>H 7.31<br>N 13.46 | 74.72<br>7.35<br>13.37 | $C_{26}H_{30}N_4O$<br>$0.1H_2OS$ |
| 45 | H | 6-methyl-pyridin-2-yl-CH2 | H | H | H | H | 242–4 | C 66.79<br>H 5.26<br>N 19.47 | 66.79<br>4.97<br>19.26 | $C_{20}H_{17}N_5O$<br>$0.9H_2O$ |
| 46 | cyclopentyl-CH2 | 2,6-diisopropyl-4-methylcyclohexyl-CH2 | H | H | H | H | 95–103 | C 73.76<br>H 8.43<br>N 11.86 | 73.83<br>8.25<br>11.65 | $C_{29}H_{38}N_4O$<br>$0.75H_2O$ |
| 47 | isopropyl | cyclohexyl-CH2 | OCH3 | H | H | OH | 235–37 | C 68.22<br>H 7.15<br>N 13.26 | 67.86<br>7.23<br>13.09 | $C_{24}H_{30}N_4O_3$ |
| 48 | isopropyl | cyclohexyl | OCH3 | H | H | Cl | 171–3 | C 65.32<br>H 6.62<br>N 12.78<br>Cl 8.10 | 64.96<br>6.78<br>12.51<br>8.47 | $C_{24}H_{29}N_4O_2Cl$ |

TABLE D-continued

| Example | R₁ | R₂ | R₃ | R₄ | R₅ | R₆ | M pt (°C.) | Analysis Calcd. | Found | Molecular Formula |
|---|---|---|---|---|---|---|---|---|---|---|
| 49 | isopropyl | cyclohexyl | OCH₃ | H | H | OCH₃ | 212–14 | C 66.71<br>H 7.50<br>N 12.40 | 66.53<br>7.25<br>12.26 | C₂₅H₃₂N₄O₃<br>0.75H₂O |
| 50 | cyclopentyl | 3-methylcyclohexyl | H | OCH₃ | H | H | 226–8 | C 72.60<br>H 7.67<br>N 12.54 | 72.28<br>7.65<br>12.44 | C₂₇H₃₄N₄O₂ |
| 51 | cyclopentyl | 3-methylcyclohexyl | OCH₃ | H | H | H | 186–8 | C 72.60<br>H 7.67<br>N 12.54 | 72.21<br>7.91<br>12.28 | C₂₇H₃₄N₄O₂ |
| 52 | cyclopentyl | cyclohexyl | OCH₃ | OCH₃ | H | H | 214–16 | C 69.29<br>H 7.45<br>N 11.97 | 69.01<br>7.42<br>11.86 | C₂₇H₃₄N₄O₃<br>0.3H₂O |
| 53 | cyclopentyl | cyclohexyl | Br | OCH₃ | OCH₃ | H | 191–3 | C 57.95<br>H 6.38<br>N 10.01<br>Br 14.3 | 67.56<br>6.01<br>9.93<br>15.8 | C₂₇H₃₃N₄O₃Br<br>1H₂O |
| 54 | cyclopentyl | 2-methylcyclohexyl | Br | H | OCH₃ | H | 167–70 | C 60.67<br>H 6.41<br>N 10.48<br>Br 14.95 | 60.47<br>6.24<br>10.00<br>14.57 | C₂₇H₃₅M₄O₂Br<br>0.5H₂O |
| 55 | isopropyl | cyclohexyl | OMe | H | H | H | 210–13 | C 64.41<br>H 7.09<br>N 12.52<br>Cl 7.92 | 64.40<br>7.34<br>12.43<br>8.0 | C₂₄H₃₁N₄ClO₂<br>0.25H₂O |

EXAMPLE 56

Preparation of
5-[4{-(N-isopropyl,N-3-methylcyclopentyl)
carboxamido}benzyl]imidazo[4,5-c]pyridine

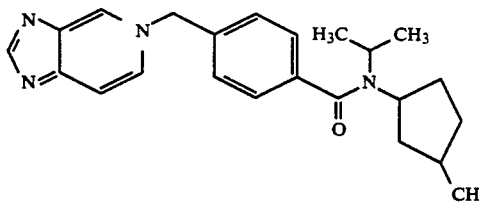

To a stirred solution of imidazopyridine (689 mg, 5.76 mmol) in N,N-dimethylacetamide (30 ml), 4-bromomethyl-N-isopropyl,N-3-methylcyclohexyl benzamide (2.17 g, 6.42 mmol) was added. The reaction mixture was stirred under argon at 95° C. After 48 h, the reaction flask was cooled to room temperature and the solvent removed under reduced pressure at <45° C. The residue obtained was triturated with ether (2×100 ml) and filtered. The crude (2.97 g) was chromatographed (silica gel, $CH_2Cl_2$—MeOH—$NH_4OH$ 90-10-1) to give pure product (0.93 g, 43%) which was recrystallized from EtOAc-$CH_3CN$. The resulting product had the following properties: mp 229°-31° C. Anal calcd. for $C_{23}H_{28}N_4O$: C, 73.40; H, 7.45; N, 14.89. Found C, 73.13; H, 7.64; N, 14.85

EXAMPLE 57

Preparation of 5-[4{-(N-isopropyl,N-cyclohexyl) carboxamido}-2-methoxybenzyl]imidazo[4,5-c]pyridine

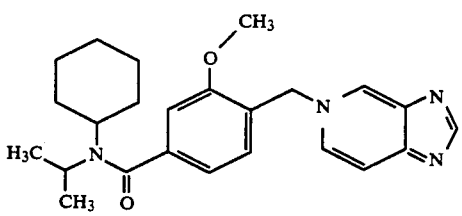

To a stirred solution of imidazopyridine (1.5 g, 12.6 mmol) in dimethylacetamide (120 ml) under argon, N-isopropyl, N-cyclohexyl-3-methoxy-4-bromomethyl-benzamide (5.1 g, 13.86 mmol) was added in one portion. The reaction temperature was slowly raised to 80°-85° C. and was stirred over the week-end. The reaction flask was cooled to room temperature and the solvent removed under reduced pressure at <45° C. The residue obtained wa triturated with excess of dry ether (2×100 ml) and filtered. The crude product was chromatographed (silica gel; $CH_2CL_2$: MeOH:$N$-$H_4OH$:: 90:10:1) to give pure alkylated product (3.53 g, 69%). The product was recrystallized from ethyl acetate. The resulting product had the following properties: mp 192°-95° C. Anal calcd. for $C_{24}H_{30}N_4O_2$: C, 70.90; H, 7.44; N, 13.78. Found C, 70.58; H, 7.43; N, 13.78.

EXAMPLE 58

Preparation of
5-[4{-(N-isopropyl,N-cyclohexyl)carboxamido}-2-methoxybenzyl]-imidazo}4,5-c]pyridine hydrochloride

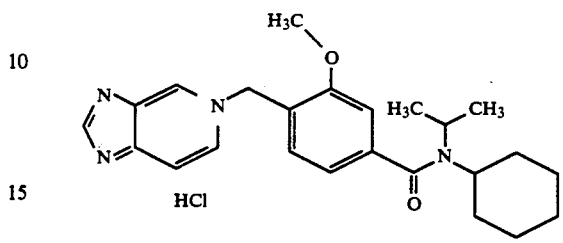

To a clear solution of the product of Example 57 (100 mg) in methanol (7 ml), HCl in dioxane (5 ml, 6N solution) was added. After stirring at room temp. for 2 h, the solvent was removed under reduced pressure. Ethyl acetate (25 ml) was added and mixture was refluxed for 1 h. The contents were filtered hot and the residue was washed with more hot ethyl acetate. After drying, the product (92 mg) was collected. The resulting product had the following properties: mp 210°-13° C.; Anal calcd. for $C_{24}H_{31}N_4ClO_2$ 0.25$H_2O$: C, 64.41; H, 7.09; N, 12.52; Cl, 7.92. Found C, 64.40; H, 7.34; N, 12.43, Cl, 8.0.

EXAMPLE 59

Preparation of
5-[4{-(N-cyclopentyl,N-3-methylcyclohexyl) carboxamido}-3-methoxybenzyl]imidazo]4,5-c]pyridine

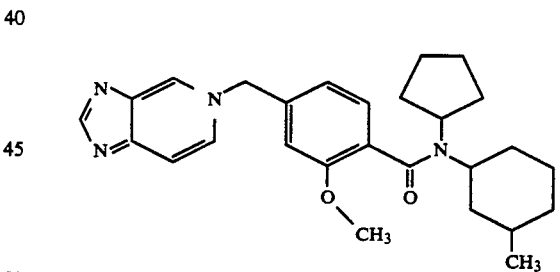

To a stirred solution of imidazopyridine (412 mg, 3.47 mmol) in N,N-dimethylacetamide (25 ml), 4-bromomethyl-2-methoxy-N-cyclopentyl, N-3-methyl-cyclohexyl benzamide (1.49 g, 3.65 mmol) was added. The reaction mixture was stirred under argon at 90°-95° C. After 48 h, the reaction flask was cooled to room temperature and the solvent removed under reduced pressure at <45° C. The residue obtained was triturated with ether (2×70 ml) and filtered. The crude (1.85 g) was chromatographed (silica gel, $CH_2Cl_2$-MeOH-$NH_4OH$ 90-10-1) to give pure product (1.05 g, 67%) which was recrystallized from EtOAc. The resulting product had the following properties: mp 226°-28° C.; Anal calcd. for $C_{27}H_{34}N_4O_2$: C, 72.60; H, 7.67; N, 12.54. Found C, 72.28; H, 7.65; N, 12.44.

EXAMPLE 60

Preparation of 5-[4{-(N-cyclopentyl,N-3-methylcyclohexyl)carboxamido}-2-methoxybenzyl]imidazo[4,5-c]pyridine

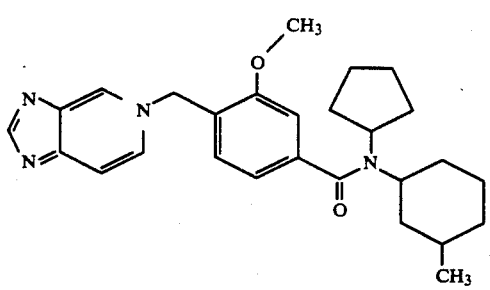

To a stirred solution of imidazopyridine (525 mg, 4.4 mmol) in N,N-dimethylacetamide (25 ml), 4-bromomethyl-3-methoxy-N-cyclopentyl, N-3-methylcyclohexyl benzamide (1.9 g, 4.66 mmol) was added. The reaction mixture was stirred under argon at 90°-95° C. After 48 h, the reaction flask was cooled to room temperature and the solvent removed under reduced pressure at <45° C. The residue obtained was triturated with ether (2×100 ml) and filtered. The crude was chromatographed (silica gel, $CH_2Cl_2$—MeOH—$NH_4OH$ 90-10-1) to give pure product (1.39 g, 71%) which was recrystallized from EtOAc-$CH_3CN$. The resulting product had the following properties: mp 186°-88° C.; Anal calcd. for $C_{27}H_{34}N_4O_2$: C, 72.60; H, 7.67; N, 12.54. Found C, 72.21; H, 7.91; N, 12.28.

EXAMPLE 61

Preparation of 5-[4{-(N-cyclopentyl,N-cyclohexyl)carboxamido}-2-methoxybenzyl]imidazo[4,5-c]-pyridine

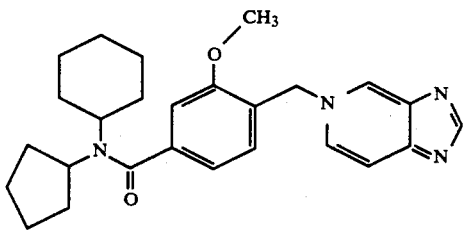

To a stirred solution of imidazopyridine (660 mg, 5.57 mmol) in N,N-dimethylacetamide (25 ml), 4-bromomethyl-2-methoxy-N-cyclopentyl,N-cyclohexyl benzamide (2.0 g, 5.07 mmol) was added. The reaction mixture was stirred under argon at 75° C. After 24 h, the reaction flask was cooled to room temperature and the solvent removed under reduced pressure. The residue obtained was diluted with water (650 ml) and basified with aq. ammonium hydroxide (20 ml). The reaction solution was extracted with chloroform (4×100 ml). The organic layer was washed with brine (3×250 ml), dried ($MgSO_4$) and filtered. The combined filtrate was concentrated and the residue (2.79 g) chromatographed (silica gel, $CHCl_3$-EtOH-$NH_4OH$ 10-90-1) to give desired product (1.36 g, 62%). The resulting product had the following properties: mp 197°-99° C.; Anal calcd. for $C_{26}H_{32}N_4O_2 0.4H_2O$: C, 71.01; H, 7.52; N, 12.74. Found C, 70.87; H, 7.49; N, 12.70.

EXAMPLE 62

Preparation of 5-[4{-(N-isopropylyl,N-cyclohexyl)carboxamido}benzyl]imidazo[4.5-c]pyridine

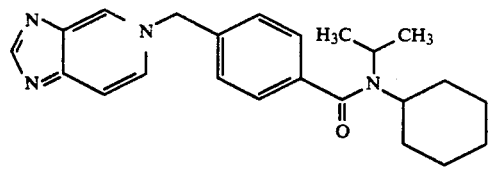

To a stirred solution of imidazopyridine (680 mg, 5.8 mmol) in N,N-dimethylacetamide (30 ml), 4-bromomethyl-N-isopropyl,N-cyclohexyl benzamide (2.2 g, 6.44 mmol) was added. The reaction mixture was stirred under argon at 80°-85° C. After 20 h, the reaction flask was cooled to room temperature and the solvent removed under reduced pressure at <45° C. The residue obtained was triturated with ether and filtered. The crude (1.85 g) was chromatographed (silica gel, $CH_2Cl_2$-EtOH-$NH_4OH$ 80-20-1) to give pure product (1.29 g, 59%) which was recrystallized from EtOAc-$CH_3CN$. The resulting product had the following properties: mp 209°-10° C. Anal calcd. for $C_{23}H_{28}N_4O$ $0.2H_2O$: C, 72.70; H, 7.48; N, 14.75. Found C, 72.92; H, 7.60; N, 14.82.

EXAMPLE 63

Preparation of 5-[4-{(N-cyclohexyl,N-isopropyl)carboxamido}-2-methoxybenzyl]-4-chloro-imidazo[4,5-c]pyridine

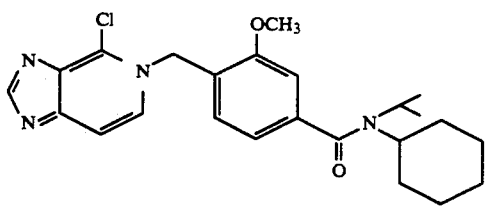

Preparation of the 4-chloro-imidazo [4,5-c]pyridine starting material as well as the 2-methoxy-3-bromobenz(N-cyclohexyl,N-isopropyl)amide have been described earlier in this specification. Coupling of the 4-chloroimidazo[4,5-c]to the 2-methoxy-3-bromobenz-(N-cyclohexyl,N-isopropyl)amide in dimethylacetamide at 85° 90° for 26 h gives the titled compound.

EXAMPLE 64

Preparation of

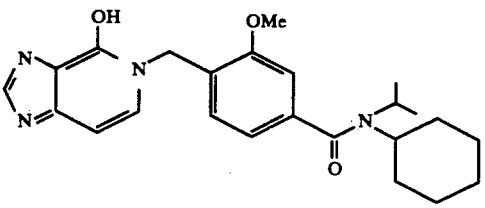

and

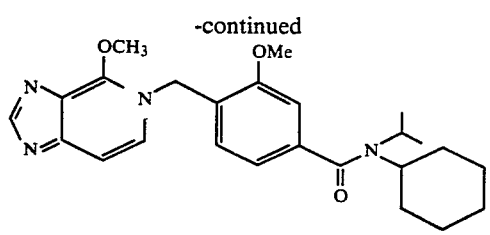

The above compounds can be synthesized according to the following scheme:

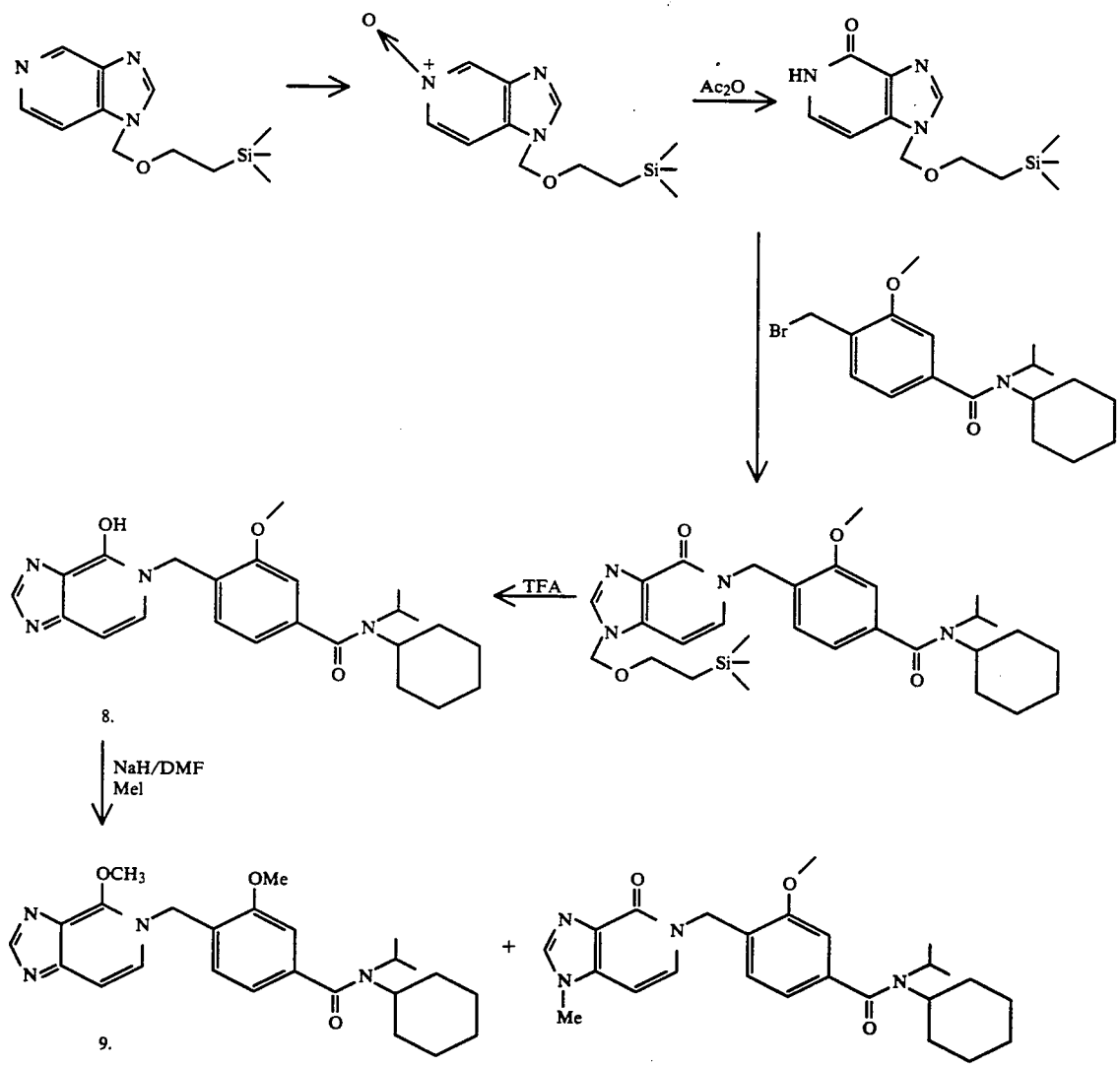

The N-1 compound of imidazolpyridine is protected by SEM-Cl and converted to a pyridine N-oxide using m-chloroperbenzoic acid in a manner described for the preparation of 4-chloro-imidazo[4,5-c]pyridine. The pyridine-N-oxide compound is refluxed in acetic anhydride for 4 hrs. to give 4-oxo-1-(2-trimethylsilyl)ethoxymethylimidazo[4,5-c]pyridine. Reacting this compound with 4-bromomethyl-3-methoxy-benz-[N-isopropyl,N-cyclohexyl] amide in dimethylformamide and sodium hydride at room temperature for 4 hours gives the 5-benzylated product. Clevage of the SEM-group is accomplished by trifluoroacetic acid at 50° C. for 18 hours to give the compound of formula 8 (titled compound). Treatment of the 4-hydroxy group of the compound of formula 8 with sodium hydride/iodomethane gives the compound of formula 9 (titled compound).

Example 65

Preparation of N-cyclopentyl-N-(3,5-dimethylcyclohexyl)-4-(5H-imidazo[4,5-c]pyridin-5-ylmethyl)-2-methoxybenzamide

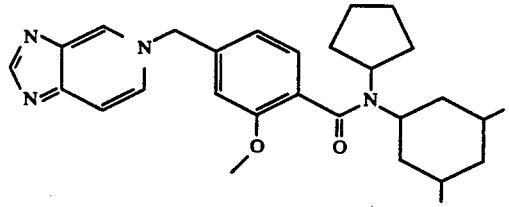

To a stirred solution of imidazopyridine (46 mg, 0.38 mmol) in N,N-dimethylformamide (10 mL), 4-bromomethyl-2-methoxy-N-cyclopentyl,N-3,5-dimethylcyclohexyl benzamide (162 mg, 0.38 mmol) was added. After stirring at room temperature for 18 hr, the solvent was removed under reduced pressure at <45° C. The residue was chromatographed (silica gel, CH2Cl2/MeOH/NH4OH 90/10/1) to give the title compound (143 mg, 78%). The resulting product has the following properties: mp 218°-20° C.; Anal calcd. for C28H36N4O2·1.3H2O: C, 69.48; H, 8.04; N, 11.57. Found C, 69.46; H, 7.74; N, 11.51.

EXAMPLE 66

Preparation of

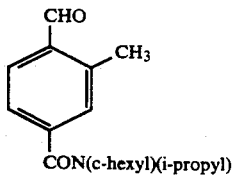

4-Bromo-3-methyl N-isopropyl cyclohexyl amide (4 g, 0.011 moles) was dissolved in 40 mls of dry THF and cooled to −60°. t-Butyllithium (13 mls of 1.7M solution) was added and the reaction was stirred for 15 minutes under argon. DMF (804 mg) was added and the reaction mixture allowed to warm to 0° over 30 minutes. After stirring at 0° for 15 minutes, the reaction mixture was poured into 1N HCl and extracted with ethyl acetate. After drying the organic layer (Na2SO4) and removal of solvent, the residue was chromatographed on silica gel using 20% ethyl acetate/hexane as the eluent to give 1.75 g (50%) of the title product. m.p.=57°-59° C.

Preparation of

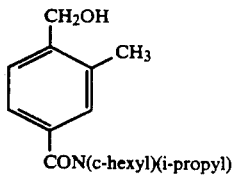

The aldehyde described above (1.70 g, 0.0052 moles) described above was dissolved in 20 mls of MeOH and cooled to 0° C. under argon. NaBH4 (110 mg) was added and the mixture was allowed to warm to 25° C. Excess solvent was removed under vacuum and the residue was treated with water and ethyl acetate. The organic layer was separated and dried (NaSO4). Removal of the solvent on the rotary evaporator gave a residue which was chromatographed on silica gel using 30% ethyl acetate/hexane as the eluent to give 1.75 g (96%) of the title compound as an oil.

Preparation of

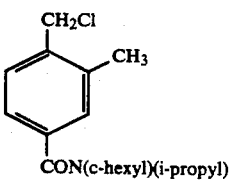

The above described benzyl alcohol (1.72 g, 0.005 moles) in 20 mls of thionyl chloride was warmed to 45° C. for 1 hour. Excess thionyl chloride was stripped off on the rotary evaporator. The residue was dissolved in ethyl acetate and washed with dilute aqueous NaHCO3 solution and water. After drying (MgSO4) and removal of solvent, the chloride was isolated as a crude oil which weighed 1.63 g (85%). C20H28NOCl M.W.=333.90 Calc: C, 71.94; H, 8.45; N, 4.19; Cl, 10.62. Found: C, 71.98; H, 8.54; N, 4.18; Cl, 10.45.

Preparation of
N-cyclohexyl-N-cyclopentyl-4-(5H)-imidazo[4,5-c]pyridin-5-ylmethyl)-3-methylbenzamide

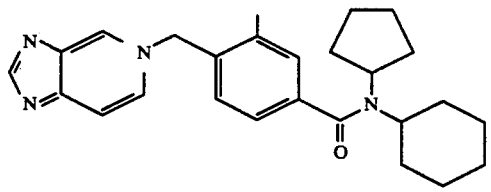

A solution of the above described benzyl chloride (500 mg, 0.0015 moles) and imidazopyridine (200 mg) in dry DMF (7 mls) was stirred overnight at 25° C. under a nitrogen atmosphere. After warming the reaction mixture to 60° C. for 3 hours to complete the reaction, the solvent was removed in vacuo using the rotary evaporator. The residue was dissolved in 25 mls of methylene chloride, washed with dilute NH4OH (10 mls) and dried (Na2SO4). After removal of the solvent, the residue was chromatographed on silica gel (20 g) using 90/10/1 CH2Cl2:MeOH:NH4OH to yield 220 mg (23%) of the title compound. The resulting product has the following properties: m.p. 189°-191° C. Anal. calcd. for C26H32N4O·1H2O. Calc: C, 7.198; H, 7.89; N, 12.89. Found: C, 72.23; H, 7.72; N, 12.47.

EXAMPLE 67

PAF-induced platelet aggregation and secretion: Washed, [$^3$H]serotonin-labeled rabbit platelets were prepared as previously described in COX, C. P., J. LINDEN and S. I. SAID: VIP elevates platelet cyclic AMP (cAMP) levels and inhibits in vitro platelet activation induced by platelet-activating factor (PAF). Peptides 5:25-28, 1984, and maintained in an atmosphere of 5% CO2 at 37° C. until used in the bioassay. Aliquots of platelets (2.5×10$^8$/ml) were incubated with either an antagonist of PAF or the appropriate vehicle for 60 sec prior to the addition of PAF (0.2 nM to 0.2 mM). Aggregation was continuously monitored on a strip-chart recorder and recorded as the height of the tracing at 60 sec after the the addition of PAF. Secretion of [$^3$H]serotonin was measured in a sample of the platelet suspension removed at 60 sec after the addition of PAF. The percent inhibition of aggregation and secretion was calculated by comparing antagonist-treated platelets with the appropriate vehicle-treated control platelets. Each combination of antagonist and PAF was repeated 12-15 times, using several different platelet preparations. IC50 values were determined by inspection of the dose-response curves.

EXAMPLE 68

Inhibition of $^3$H-PAF Binding to Human Platelet Membrane Receptors

Receptor Preparation: Ten units of in-dated human packed platelets, each containing 45-65 ml platelet rich-plasma, were purchased from a commercial blood bank. Disposable plasticware was used throughout for receptor preparation. The units were pooled and a 1 ml aliquot was removed for determination of platelet concentration, using a Coulter Counter. The remaining platelet rich plasma was dispensed into 50 ml conical tubes and centrifuged at room temperature for 15 minutes at 3000 RPM (2300×g). Plasma was decanted and the platelets were resuspended in 35 ml of buffer 10 mM Trizma 7.0, 2 mM EDTA (dipotassium salt), and 150 mM KCl and transferred to fresh tubes, which were centrifuged again as above. The platelets were washed 3 times, avoiding contaminating erythrocytes at the bottom of the pellets. Pellets were consolidated at each step, and by the last wash with EDTA/KCl buffer, most of the erythrocytes were in 1 tube. The pellets were resuspended in buffer containing 10 mM Trizma 7.0 with 10 mM $CaCl_2$. Following centrifugation, the buffer was decanted and the pellets were resuspended in the $CaCl_2$ buffer, avoiding erythrocyte contamination by recovering less than 100% of the platelet pellets. The resuspended platelets were dispensed in 8–10 ml aliquots into Corex tubes and disrupted by three cycles of freezing (dry ice/ethanol) and thawing (24° C.). The tubes were centrifuged at 40,000×g for 20 minutes at 4° C. Supernatants were decanted and each pellet was resuspended in 5–7 ml 10 mM Trizma 7.0. All resuspended pellets were pooled and aliquots of about 1200 ml were dispensed into 1.5 ml microfuge tubes and frozen at −70° C. Protein content was determined by a fluorescamine protein assay.

Assay Methods: Receptor Characterization—Each receptor preparation was evaluated to determine the number of receptor populations, the number of PAF receptor equivalents/mg protein and the dissociation constant ($K_D$) for PAF binding. This required 2–3 experiments in which the protein concentration was held constant and the $^3$H-PAF ligand concentration was varied from approximately 0.10–2.5 nM and the data was analyzed by Scatchard methodology. Total incubation volume was 250 ml for these procedures and incubations were conducted at 24° C. for 30 minutes. For further experimentation, total incubation volumes are 500 ml. Protein and ligand concentrations were adjusted to give 0.075 nM receptor equivalents in the presence of 0.75 nM $^3$H-PAF. Each receptor preparation was then used to determine the dose—response displacement relationship of unlabeled PAF and the PAF antagonist, triazolam. As long as the $K_D$ value and $IC_{50}$ values for PAF and triazolam were consistent with similar data collected from past receptor preparations used in the assay, the new receptor preparation was used for evaluating compounds.

Assay Methods: Routine Assay of Compounds—The compounds were weighed precisely and solubilized in quantities of DMSO such that a 5 ml aliquot in the incubate would deliver the desired compound concentration. Compounds tested for the first time in this assay were evaluated at a concentration of 50 mM in the incubation medium. All compounds were generally solubilized in DMSO for about 2 hours prior to assay. Triazolam was always included in each screening assay as a compound inhibition control. A standard concentration of 50 mM inhibited $^3$H-PAF binding by approximately 50%. Nonspecific binding control solution was made by drying to completion about 26.2 ml unlabeled PAF under a stream of argon. PAF was resolubilized in 1000 ml DMSO. When delivered in a 5 ml aliquot, the final concentration of 1 mM PAF in the incubate exceeded by 1000-fold the concentration of $^3$H-PAF.

All buffers containing proteins were made at room temperature on the day of assay. Assay buffer was prepared by adding 125 mg human albumin to 25 ml of stock buffer (10 mM Trizma 7.4 with 20 mM $CaCl_2$). Rinse buffer was made by adding 20 grams bovine serum albumin to 1000 ml stock buffer. About 80 ml of rinse buffer was decanted into a small pyrex dish and used to soak 65 Whatman GF/C 2.5 cm glass filters. The remaining rinse buffer was poured into a repipet and placed into an ice bath along with the filters.

Ligand for assay was prepared by adding about 10 ml of stock $^3$H-PAF (DuPont NEN, NET-668) to 14 ml of assay buffer. Since the amount of $^3$H-PAF in the final incubate was to be 0.75 nM, the actual amount of stock $^3$H-PAF to be used had to be determined for each lot of material based upon its specific activity.

Membrane receptors for assay were prepared by thawing the appropriate number of tubes at room temperature and adding membranes to 10 mM Trizma 7.0 containing 10 mM $CaCl_2$. A total volume of 14 ml was made. The actual amount of membranes needed was determined by the requirement to have 0.075 nM PAF receptor equivalents per assay tube. All materials were kept in motion by rocking on a rocker plate.

First, 5 ml of compound or DMSO was added to each 12×75 mm polypropylene tube, followed by the addition of 95 ml assay buffer. Next, 200 ml $^3$H-PAF was added to each tube and 3 aliquots of $^3$H-PAF taken at different times during the dispensing were placed in scintillation vials.

The reaction was initiated by the addition of 200 ml of membranes. All tubes were very briefly vortexed and placed in a 24° C. water bath for about 30 minutes. During this time, Whatman GF/C filters were placed on the filter racks of 5 Millipore vacuum manifolds. The incubations were terminated by first adding 4 ml ice-cold rinse buffer to each incubation tube and then decanting them over the filters under vacuum. Tubes and filters were rinsed twice more. Each filter was placed into a 20 ml scintillation vial to which 20 ml Aquasol (DuPont NEN, NDF 952) was added. All vials were given 2 hours in the dark for photo and chemiluminence to dissipate prior to liquid scintillation counting.

In summary, each incubation tube contained 500 ml total volume of incubate. This consisted of 5 ml drug with DMSO or only DMSO, 95 ml assay buffer, 200 ml $^3$H-PAF (0.75 nM final concentration) and 200 microleters membrane receptors (0.075 nM final concentration). 60 tubes per assay were run and each dose was performed in triplicate. Controls in every assay consisted of 2 diluent (DMSO) "0" controls (2 triplicate determinations placed at different positions within the 60 tube assay), 1 nonspecific binding control, and 1 triazolam drug control. The 16 remaining doses were used to test 16 different compounds at the screening dose of 50 mM, or to run dose-response determinations for a compound. In general, dose-response curves were composed of 4 compound doses designed to inhibit $^3$-PAF binding by 15-85%, with at least 1 dose on each side of the 50% point.

Routine Assay Calculations: Triplicate DPM determinations (corrected for background) within a single compound dose were averaged while all 6 determinations of total binding ("0" dose, DMSO only) were averaged. The amount for nonspecific binding (1 mM PAF) was subtracted from all the dose averages, giving an amount of specific binding in all cases. The percent displacement of $^3$H-PAF or inhibition of binding was calculated by the formula $STBo-SBc/STBo \times 100$, where $STBo$ = specific binding of "0" dose controls and $SBc$ = specific binding in the presence of compound. If a compound tested at the initial screening dose of 50 mM inhibited binding by 45% or more, the compound was considered active and was tested in a dose-response manner to determine an $IC_{50}$ value.

Compounds inhibiting PAF binding by less than 45% at a 50 mM concentration were considered inactive and no further testing was done.

$IC_{50}$ values were determined on active compounds in subsequent tests. Three or more compound doses must inhibit $^3$H-PAF binding between 15–85%. Using a computer program, % displacement data was transformed (logit) and a least squares linear regression was performed on the data meeting the 15–85% requirement to determine $IC_{50}$ values from data points derived from the same assay.

| Compound | PAF induced platelet secretion ($IC_{50}$)M | PAF induced platelet aggregation ($IC_{50}$)M | Inhibition of $^3$H-PAF Binding to Human Platelet ($IC_{50}$) $\mu$M |
|---|---|---|---|
| 5-[4-(N-methyl-N-cyclohexylcarboxamido)benzyl]imidazo[4,5-c]pyridine | $7.2 \times 10^{-7}$ | $10^{-5}$ to $10^{-6}$ | 15.2 |
| 5-[4-(N-n-octylcarboxamido)benzyl]imidazo[4,5-c]pyridine | $10^{-6}$ to $10^{-7}$ | $10^{-5}$ to $10^{-6}$ | 11.0 |
| 5-[4-(N-n-decylcarboxamido)benzyl]imidazo[4,5-c]pyridine | $10^{-6}$ to $10^{-7}$ | $10^{-5}$ to $10^{-6}$ | 9.71 |
| 5-[4-(N-n-dodecylcarboxamido)benzyl]imidazo[4,5-c]pyridine | 1 to $5 \times$ to $10^{-7}$ | $10^{-6}$ to $10^{-7}$ | 11.9 |
| 5-[4-(N-2-decalyl-N-methylcarboxamido)benzyl]imidazo[4,5-c]pyridine | $10^{-6}$ | $10^{-5}$ to $10^6$ | 13.2 |
| 5-[4-(N-2(2,4,4-trimethyl)pentyl carboxamide)benzyl]imidazo[4,5-c]pyridine | $10^{-6}$ | $10^{-5}$ | 22.3 |
| 5-[4-(N,N-diisopropyl carboxamido)benzyl]imidazo[4,5-c]pyridine | $10^{-7}$ to $10^8$ | $10^{-5}$ to $10^{-6}$ | 7.65 |
| 5-[4-(N,N-dicyclopentyl carboxamido)benzyl]imidazo[4,5-c]pyridine | $10^{-8}$ to $10^{-9}$ | $10^{-7}$ to $5 \times 10^{-8}$ | 0.31 |
| 5-[4-(N-cyclohexylcarboxamido)benzyl]imidazo[4,5-c]pyridine | $10^{-6}$ to $10^{-7}$ | $10^{-5}$ | 19.3 |
| 5-[4-(N-ethyl-N-cyclohexyl carboxamido)carboxamido)benzyl]imidazo[4,5-c]pyridine | $10^{-7}$ to $10^{-6}$ | $10^{-6}$ to $10^{-5}$ | 5.20 |
| 5-[4-(N-isopropyl-N-cyclohexyl carboxamido)benzyl]imidazo[4,5-c]pyridine | $10^{-8}$ | $10^{-7}$ to $10^{-8}$ | 0.17 |
| 5-[4-(N-sec.butyl-N-cyclohexylcarboxamido)benzyl]imidazo[4,5-c]pyridine | $10^{-8}$ to $10^{-9}$ | $10^{-7}$ to $5 \times 10^{-8}$ | 0.58 |
| 5-[4-(N-isobutyl-N-cyclohexylcarboxamido)benzyl]imidazo[4,5-c]pyridine | $10^{-7}$ | $10^{-6}$ | 2.82 |
| 5-[4-(N-3-pentyl-N-cyclohexylcarboxamido)benzyl]imidazo[4,5-c]pyridine | $10^{-7}$ to $10^{-8}$ | $10^{-6}$ to $10^{-7}$ | — |
| 5-[4-(N-cyclopropyl-N-cyclohexylcarboxamido)benzyl]imidazo[4,5-c]pyridine | $10^{-6}$ to $10^{-7}$ | | 3.68 |
| 5-[4-(N-cyclobutyl-N-cyclohexylcarboxamido)benzyl]imidazo[4,5-c]pyridine | $10^{-8}$ to $10^{-9}$ | $10^{-7}$ to $10^{-8}$ | 0.0199 |
| 5-[4-(N-cyclopentyl-N-cyclohexylcarboxamido)benzyl]imidazo[4,5-c]pyridine | $10^{-8}$ to $10^{-9}$ | $10^{-7}$ to $10^{-8}$ | 0.32 |
| 5-(4-(N,N-dicyclohexyl carboxamidobenzyl)imidazo[4,5-c]pyridine | $10^{-8}$ | $10^{-6}$ to $10^{-7}$ | 1.06 |
| 5-[2-[4-(N-methyl-N-cyclohexylcarboxamido)phenyl]ethyl]imidazo[4,5-c]pyridine | $10^{-5}$ to $10^{-6}$ | $10^{-4}$ to $10^{-5}$ | — |
| 5-[3-[4-(N-methyl-N-cyclohexylcarboxamido)phenyl]propyl]imidazo[4,5-c]pyridine | $10^{-5}$ to $10^{-6}$ | $10^{-4}$ to $10^{-5}$ | 61.1 |
| 5-[4-(N,N-dicyclopentyl carboxamido)-2-methoxybenzyl] | $10^{-8}$ to $10^{-9}$ | $10^{-7}$ to $10^{-8}$ | 0.055 |

-continued

| Compound | PAF induced platelet secretion (IC$_{50}$)M | PAF induced platelet aggregation (IC$_{50}$)M | Inhibition of $^3$H-PAF Binding to Human Platelet (IC$_{50}$) μM |
|---|---|---|---|
| imidazo[4,5-c]pyridine 5-[4-(N-cyclohexyl-N-cyclopentylcarboxamido)-2-methoxybenzyl]imidazo [4,5-c]pyridine | $10^{-8}$ to $10^{-9}$ | $10^{-8}$ | 0.0302 |
| 5-[4-(N-isopropyl-N-cyclohexylcarboxamido)2-methoxybenzyl]imidazo [4,5-c]pyridine | $10^{-8}$ | $10^{-7}$ to $10^{-8}$ | 0.0665 |
| 5-[4-(N-methyl-N-cyclohexyl carboxamido)-2-methoxybenzyl] imidazo[4,5-c]pyridine | $10^{-6}$ to $10^{-7}$ | $10^{-5}$ to $10^{-6}$ | — |
| 5-[4-(N-cyclopentyl-N-cyclohexylcarboxamido)-2-fluorobenzyl]imidazo [4,5-c]pyridine | $10^{-8}$ to $10^{-9}$ | $10^{-7}$ to $10^{-8}$ | 0.0755 |
| 5-[4-(N-isopropyl-N-cyclohexyl carboxamido)-2-fluorobenzyl] imidazo[4,5-c]pyridine | $10^{-7}$ to $10^{-8}$ | $10^{-7}$ to $10^{-8}$ | 0.442 |
| 5-[4-(N-methyl-N-cyclohexyl carboxamido)-2-fluorobenzyl] imidazo[4,5-c]pyridine | $10^{-6}$ to $10^{-7}$ | $10^{-5}$ to $10^{-6}$ | — |
| 5-[4-(N-tert.butyl-N-cyclohexylcarboxamido) benzyl]imidazo [4,5-c]pyridine | $10^{-8}$ to $10^{-9}$ | $10^{-7}$ to $10^{-8}$ | 87.7% inhib (50 μM) |
| 5-[4-(N-phenyl-N-cyclopentylcarboxamido) benzyl]imidazo [4,5-c]pyridine | $10^{-6}$ to $10^{-7}$ | $10^{-6}$ | 2.35 |
| 5-[4-(N-3-methylcyclohexyl-N-cyclopentylcarboxamido)benzyl] imidazo[4,5-c]pyridine | $10^{-8}$ to $10^{-9}$ | $10^{-7}$ to $10^{-8}$ | 0.074 |
| 5-[4-(N-4-methylcyclohexyl-N-cyclopentylcarboxamido)benzyl] imidazo[4,5-c]pyridine | $10^{-7}$ to $10^{-8}$ | $10^{-6}$ to $10^{-7}$ | 0.75 |
| 5-[3-(N-methyl-N-cyclohexyl carboxamido)benzyl]imidazo [4,5-c]pyridine | $10^{-4}$ to $10^{-5}$ | $10^{-4}$ to $10^{-5}$ | 38% inhib (50 μM) |
| 5-[3-(N-isopropyl-N-cyclohexyl carboxamido)benzyl]imidazo [4,5-c]pyridine | $10^{-5}$ to $10^{-6}$ | $10^{-4}$ to $5 \times 10^{-5}$ | 26.1% inhib (50 μM) |
| 5-[4-(N,N-dicyclopentyl carboxamido)benzyl]-4-methylimidazo[4,5-c]pyridine | $10^{-7}$ to $10^{-8}$ | $10^{-7}$ to $10^{-8}$ | 0.188 |
| 5-[4-(N,N-dicyclopentyl carboxamido)benzyl]-2-methylimidazo[4,5-c]pyridine | $10^{-6}$ to $10^{-7}$ | $10^{-5}$ to $10^{-6}$ | 70.8% inhib (50 μM) |
| N-cyclopentyl-N-(3,5-dimethyl cyclohexyl)-4-(5H-imidazo[4,5-c] pyridin-5-ylmethyl)-2-methoxybenzamide | $10^{-9}$ | | 0.001 |
| N-cyclohexyl-N-cyclopentyl-4-(5H-imidazo[4,5-c] pyridin-5-ylmethyl)-3-methylbenzamide | $2 \times 10^{-9}$ | | 0.018 |

What we claim is:

1. A compound which is N-cyclopentyl-N-(3,5-dimethylcyclohexyl)-4-(5H-imidazo[4,5-c]pyridin-5-ylmethyl)-2-methoxybenzamide.

2. A pharmaceutical composition useful for treating diseases or disorders mediated by platelet-activating factor comprising an effective amount of N-cyclopentyl-N-(3,5-dimethylcyclohexyl)-4-(5H-imidazo[4,5-c]pyridin-5-ylmethyl)-2-methoxybenzamide, together with one or more non-toxic pharmaceutically acceptable carriers.

3. A method for treating diseases or disorders mediated by platelet-activating factor comprising administering a therapeutically effective dose of N-cyclopentyl-N-(3,5-dimethylcyclohexyl)-4-(5H-imidazo[4,5-c]pyridin-5-ylmethyl)-2-methoxybenzamide to a mammal in need.

4. A compound which is N-cyclohexyl-N-cyclopentyl-4-(5H-imidazo[4,5-c]pyridin-5-ylmethyl -3-methylbenzamide.

5. A pharmaceutical composition useful for treating diseases or disorders mediated by platelet-activating factor comprising an effective amount of N-cyclohexyl-N-cyclopentyl-4-(5H-imidazo[4,5-c]pyridin-5-ylmethyl)- 3-methylbenzamide together with one or more non-toxic pharmaceutically acceptable carriers.

6. A method for treating diseases or disorders mediated by platelet-activating factor comprising administering a therapeutically effective dose of N-cyclohexyl-N-cyclopentyl-4-(5H-imidazo[4,5-c]pyridin-5-ylmethyl)-3-methylbenzamide to a mammal in need.

* * * * *

UNITED STATES PATENT AND TRADEMARK OFFICE
CERTIFICATE OF CORRECTION

PATENT NO. : 5,227,384
DATED : July 13, 1993
INVENTOR(S) : Khanna, et al.

It is certified that error appears in the above-indentified patent and that said Letters Patent is hereby corrected as shown below:

Column 1, line 3, reading "5,019,581" should read -- 5,014,581 --.

Column 2, line 36, reading "1 to carbon" should read -- 1 to 6 carbon --.

Column 3, line 43, reading "having to 6" should read -- having 1 to 6 --.

Column 4, line 1, reading "group are" should read -- groups are --.

Column 4, line 12, reading "straight o branched" should read -- straight or branched --.

Column 5, line 37, reading "are defied" should read -- are defined --.

Column 7, line 54, reading "with IN HCL," should read -- with 1N HCL, --.

Column 8, line 39, reading "with he" should read -- with the --.

Column 13, line 14, reading "2-trialkylsily)" should read --2-trialkylsilyl--

Column 16, line 61, reading "to give 13.38 g" should read -- to give 3.13 g --.

UNITED STATES PATENT AND TRADEMARK OFFICE
CERTIFICATE OF CORRECTION

PATENT NO. : 5,227,384
DATED : July 13, 1993
INVENTOR(S) : Khanna, et al.

It is certified that error appears in the above-indentified patent and that said Letters Patent is hereby corrected as shown below:

Column 17, line 4, reading "5-[4-(Nmethyl-" should read -- 5-[4-(N-methyl- --.

Column 28, Ex. 44, reading "0.1 $H_2OS$" should read -- 0.1 $H_2O$ --.

Column 31, line 59, reading "wa triturated" should read -- was triturated --.

Column 32, line 37, reading "imidazo]4,5-C]" should read -- imidazo[4,5-C] --.

Column 37, line 49, reading "($NaSO_4$)" should read -- ($Na_2SO_4$) --.

Column 38, line 8, reading "-(5H)-imidazo" should read -- -(5H-imidazo --.

Column 38, line 33, reading "Calc: C, 7.198;" should read -- Calc: C, 71.98; --.

Column 38, line 45, reading "(2.5 x $10^{89}$/ml)" should read -- (2.5 x $10^8$/ml) --.

Column 39, line 7, reading "buffer 10 mM" should read -- buffer (10 mM --.

UNITED STATES PATENT AND TRADEMARK OFFICE
CERTIFICATE OF CORRECTION

PATENT NO. : 5,227,384
DATED : July 13, 1993
INVENTOR(S) : Khanna, et al.

It is certified that error appears in the above-indentified patent and that said Letters Patent is hereby corrected as shown below:

Column 40, line 6, reading "i000 ml stock" should read -- 1000 ml stock --.

Column 44, line 57, reading " -5-ylmethyl-3-" should read -- -5-ylmethyl)-3- --.

Signed and Sealed this

Tenth Day of January, 1995

Attest:

BRUCE LEHMAN

Attesting Officer

Commissioner of Patents and Trademarks